(12) United States Patent
Beckman

(10) Patent No.: US 11,433,256 B2
(45) Date of Patent: Sep. 6, 2022

(54) TREATMENT TECHNIQUES WITH REMOTE ACTIVATION OF DEVICES AND REAGENTS

(71) Applicant: Christopher V. Beckman, Los Angeles, CA (US)

(72) Inventor: Christopher V. Beckman, Los Angeles, CA (US)

( * ) Notice: Subject to any disclaimer, the term of this patent is extended or adjusted under 35 U.S.C. 154(b) by 162 days.

(21) Appl. No.: 16/900,864

(22) Filed: Jun. 12, 2020

(65) Prior Publication Data

US 2020/0306558 A1    Oct. 1, 2020

Related U.S. Application Data

(63) Continuation-in-part of application No. 15/690,267, filed on Aug. 29, 2017, now abandoned, which is a (Continued)

(51) Int. Cl.
| | |
|---|---|
| *A61N 5/10* | (2006.01) |
| *A61K 41/00* | (2020.01) |
| *A61K 9/51* | (2006.01) |
| *G16H 20/40* | (2018.01) |
| *B82Y 5/00* | (2011.01) |

(52) U.S. Cl.
CPC ............. *A61N 5/1031* (2013.01); *A61K 9/51* (2013.01); *A61K 41/0038* (2013.01); *A61N 5/1001* (2013.01); *A61N 5/1067* (2013.01); *A61N 5/1084* (2013.01); *G16H 20/40* (2018.01); *A61N 2005/1094* (2013.01); *A61N 2005/1096* (2013.01); *A61N 2005/1098* (2013.01); *B82Y 5/00* (2013.01)

(58) Field of Classification Search
CPC .. A61N 5/1031; A61N 5/1001; A61N 5/1067; A61N 5/1084; A61N 2005/1094; A61N 2005/1096; A61N 2005/1098; A61K 9/51; A61K 41/0038; G16H 20/40; G16H 40/63; G16H 40/67; B82Y 5/00; A61P 35/00

See application file for complete search history.

(56) References Cited

U.S. PATENT DOCUMENTS

2017/0265803 A1* 9/2017 Copty ................ A61K 41/0052

* cited by examiner

*Primary Examiner* — Courtney D Thomas

(57) ABSTRACT

The present invention includes new medical techniques involving radiation and electromagnetic actuation of reagents deployed and directed within bodily fluids (e.g., the bloodstream, digestive tract, or lymph ducts) of a patient. In one aspect of the invention, a medical reagent and/or particle is provided with multiple dipoles, oriented differently in three-dimensional space, allowing a remote control system to drive the acceleration and three-dimensional orientation of the medical agent or particle according to a three-dimensional path. In some embodiments, the medical reagent and/or particle is energized remotely to an activation energy level, and then driven into the treatment target. The design of each small-scale machine may include different sub-devices and electrostatic charges or magnetic dipoles, at different surface or internal locations. In some aspects, the sub-devices include actuable housings and other sub-devices, to deliver drugs or other factors at specific locations commanded by the control system or a user.

20 Claims, 20 Drawing Sheets

Related U.S. Application Data continuation-in-part of application No. 14/217,448, filed on Mar. 17, 2014, now Pat. No. 9,743,942, and a continuation-in-part of application No. 15/202,565, filed on Jul. 5, 2016, now Pat. No. 9,833,638, which is a continuation-in-part of application No. 14/612,285, filed on Feb. 2, 2015, now Pat. No. 9,381,379, which is a continuation-in-part of application No. 13/371,461, filed on Feb. 12, 2012, now Pat. No. 8,948,341.

(60) Provisional application No. 61/852,122, filed on Mar. 15, 2013.

© 2012 Christopher V. Beckman

© 2012 Christopher V. Beckman

© 2012 Christopher V. Beckman

© 2012 Christopher V. Beckman

Source Digital Language - 7 symbol/key Alphabet

Example Source Signal No. 1

Example Source Signal No. 2

Resultant Digital Language - 14 symbol/key Alphabet

Example Resultant Signal

© 2012 Christopher V. Beckman

© 2012 Christopher V. Beckman

© 2012 Christopher V. Beckman

© 2015 Christopher V. Beckman (C) 2016, Christopher V. Beckman

TREATMENT TECHNIQUES WITH REMOTE ACTIVATION OF DEVICES AND REAGENTS

CROSS-REFERENCE TO RELATED APPLICATIONS

This application is a continuation-in-part of U.S. patent application Ser. No. 15/690,267, filed Aug. 29, 2017, which itself is a continuation-in-part of U.S. patent application Ser. No. 15/202,565, filed Jul. 5, 2016, which is a continuation-in-part of U.S. patent application Ser. No. 14/612,285, filed Feb. 2, 2015, now U.S. Pat. No. 9,381,379, which is a continuation-in-part of U.S. patent application Ser. No. 13/371,461, filed Feb. 12, 2012, now U.S. Pat. No. 8,948,341. This application is also a continuation-in-part of U.S. patent application Ser. No. 14/217,448, now U.S. Pat. No. 9,743,942, which claims the benefit of U.S. Provisional Application No. 61/852,122, filed Mar. 15, 2013. The entire contents and disclosure of each of the above applications are hereby incorporated by reference in the present application, as if fully set forth herein.

Intellectual Property Notice: © 2012-2020 Christopher V. Beckman. The disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. Unless otherwise stated, all trademarks disclosed in this patent document and associated application parts and other distinctive names, emblems, and designs associated with product or service descriptions, are subject to trademark rights. Specific notices also accompany the drawings incorporated in this application; the matter subject to this notice, however, is not limited to those drawings.

FIELD OF THE INVENTION

This application relates to electromagnetic radiation and field management systems, and the application of reagents.

BACKGROUND

The field of radiation therapy (also known as "radiotherapy"), along with the sub-field of radiation oncology, seeks the control or treatment of biological processes through the use of electromagnetic radiation. Radiation therapy has been in use in some form for over a century, shortly following the discovery of X-Rays by Wilhelm Rontgen, in November of 1895. Generally speaking, radiation therapy accomplishes its goals by targeting living tissues with ionizing radiation, altering the tissue's size, structure, composition and function. For example, in cancer therapy, a beam of ionizing radiation may be focused spatially on a malignant tumor, destroying, among other things, the malfunctioning DNA which has caused it to de-differentiate from healthy to malignant tissue, and, thereby, arresting the disease process. Radiation therapy is especially useful in treating "inoperable" tumors, where the size and location create unacceptable dangers or where the prognosis for recurrence despite surgery is especially great, and surgical solutions are either deemed to be ineffective options, or to present too great a risk of injury or earlier death when weighed against the potential successful removal of the tumor.

Within the sub-field of radiation oncology, linear accelerator machines ("LINACs") that generate megavoltage X-rays for deep-tissue penetration are currently in heavy use. LINACs are a form of "external beam" radiation therapy, in the sense that they generate radiation from outside of the treatment area and patient's body, and focus it inward toward the tumor. Other forms of radiation therapy include brachytherapy and systemic radioisotopes (where the radiation source is inserted, or taken by pill or injection, respectively). Like surgical intervention, brachytherapy causes collateral damage to healthy tissue from the trauma of the procedure. Systemic radioisotopes are even more rarely used, due to difficulties in targeting tumors or other targets, and system-wide collateral damage.

Although LINACs have the advantage of avoiding some of the tissue damage and other risks of invasive surgery and brachytherapy, and can cause less damage than systemic radioisotopes, they also present their own drawbacks. In most instances, the external beam of radiation must first pass through healthy, surrounding tissues before reaching the tumor. As a result, those tissues are also damaged, by the same process that damages the tumor tissue. And because a radiation beam can ionize the DNA of any biological cell in its path, LINACs cause mutations in healthy surrounding tissue, which mutations can lead, among other things, to cancer. Thus, ironically, radiation therapy bears a probability of causing new cancer, in addition to otherwise damaging surrounding tissues, even if it succeeds at destroying a current tumor. In addition to causing more cancer, a variety of other radiation therapy side effects are seen in collaterally-damaged, otherwise healthy adjacent tissues, including edema, neural and cognitive decline, hair loss, irritation and heart disease.

In tomotherapy and multiple-source fixed LINAC machines, the radiation source may be applied at a variety of isocentric angles from outside of the treatment area—all of which target the tumor—in order to disperse less of the radiation across a greater volume of healthy tissue, such that it can withstand the impact of the radiation more easily. Beginning in the 1990s, image-guided and intensity-, spatial approach- and beam shape-modulated radiation therapy techniques have been developed, which further seek to target tumors with greater accuracy. These techniques (hereafter, called "IMRT") use advanced imaging technology and computer-aided dosage plans in conjunction with LINACs and other ionizing radiation sources, to target the diseased tissues and avoid collateral damage to more important healthy tissue with greater accuracy. For example, the RapidArc® machine, from Varian Medical Systems, Inc., employs computer modeling of 360-degree dosage plans (1) modulating the shape of the beam source through its escape aperture (via multiple collimating "leaves" that are extended or withdraw over the aperture) (2) controlling gantry (beam-emitting source) rotation speed, as well as (3) beam intensity, to deliver a more favorable dosage pattern.

Radiation therapy is often carried out over several sessions in a process called "fractionation," rather than all at once, to give healthy, non-malignant cells more of an opportunity to heal following exposure. However, the diseased tumor cells may have more of a potential to survive treatment as well, through such timing techniques. In addition, the added time needed for radiation therapy treatments is disruptive to the patients' life, as well as expensive and labor-intensive for both the patient and medical staff.

IMRTs employ a variety of particle and electromagnetic wave radiation beams. Most forms of radiotherapy have a decaying ionization profile, meaning that the particle or electromagnetic radiation beam's ionization energy tends to decrease as the beam penetrates deeper into tissue. An exception may be some forms of proton or heavier ion therapy, which exhibit what is known as a "Bragg Curve," a phenomenon where ionization beam energy peaks shortly before the particles come to rest (assuming they do not fully exit the target or collateral tissue into space). Proton therapy has been rapidly developing in the hope that these heavier ionization decay profiles will allow for greater localization of radiation dosage to tumors, while decreasing dosage to healthy tissues. However, collateral damage is a major issue in these therapies due to significant dosage to healthy collateral tissues.

It is an objective of the present invention to increase the dosage effectiveness of external radiation therapy to target tissues, while decreasing the damage to collateral tissues.

Medical devices for intravascular treatment have been in use for several decades, including angioplasty to treat atherosclerosis. In angioplasty, a balloon catheter is guided to a narrowed section of an artery or vein and then expanded to widen the lumen.

Nanorobotics and other nanotechnologies have also been under development for many years, including machines that are constructed with components on a scale at or near a nanometer scale ($10^{-9}$ meters). Somewhat larger-scale machines, including nanorobots of about 10 micrometers in length, height or depth, are often defined as nanotechnology as well, but may also be described as microscale devices. Microscale devices may also, alternatively or in addition, be defined as having a size below 1 millimeter.

It should be understood that the disclosures in this application related to the background of the invention in, but not limited to, this section titled "Background," are to aid readers in comprehending the invention, and do not set forth prior art or other publicly known aspects affecting the application; instead the disclosures in this application related to the background of the invention comprise details of the inventor's own discoveries, work and work results, including aspects of the present invention. Nothing in the disclosures related to the background of the invention is or should be construed as an admission related to prior art or the work of others prior to the conception or reduction to practice of the present invention.

SUMMARY OF THE INVENTION

The present invention includes new techniques for radiotherapy and other external (e.g., electromagnetic) influence on treatment subjects. The present invention includes new medical techniques involving radiation and electromagnetic actuation of reagents deployed and directed within bodily fluids (e.g., the bloodstream, digestive tract, or lymph ducts) of a patient. In one aspect of the invention, a medical reagent and/or particle is provided with multiple dipoles, oriented differently in three-dimensional space, allowing a remote control system to drive the acceleration and three-dimensional orientation of the medical agent or particle according to a three-dimensional path based on the surface characteristics of a treatment target within the treatment subject. In some embodiments, the medical reagent and/or particle is energized remotely to an activation energy level, and then driven into the treatment target. The design of each small-scale machine may include different sub-devices and electrostatic charges or magnetic dipoles, at different surface or internal locations. In some aspects, the sub-devices include actuable housings and other sub-devices, to deliver drugs or other factors at specific locations commanded by the control system or a user.

According to some embodiments, the small-scale machines are applied to an arterial plaque to first remove blood clots and fatty deposits. In some embodiments, which are preferred, the small-scale machines then deliver healing drugs or other factors to the cleaned lumen walls. In other methods, the small-scale machines, which do not include drugs, but do include different, selectable sub-devices, are driven into treatment targets at different orientations and angles of attach, to selectively apply the different sub-devices. In other embodiments, sub-devices within the machine are actuated to move relative the remainder of the sub-devices, to apply pinching, cutting, grinding and drug-delivery tasks. This separate actuation of the sub-devices may still be by remote actuation by the control system, mediated by the electromagnetic actuation of differential dipoles or driving chemical reactions by combining sub-devices with a reaction target, or differential radiation targeting (e.g., by heating or inducing current in specific components of the sub-devices).

In another aspect of the invention, multiple sources of radiation are provided in preferably the same or a harmonic or otherwise planned frequency and in the same superposed period and polarization with respect to one another, from the same side of a target, focused on a leading (a.k.a. proximal) structure in the target and are thereby made to interfere with one another at or near and before a target location, greatly increasing a vector sum of electromagnetic radiation wave amplitudes and ionization energy levels to the target tissue, or creating resonant, harmonic, higher energy or other critical frequencies concentrated in target-associated matter and structures.

In additional aspects of the present invention, two or more of such radiation sources create Encrypted Source Beams that, upon converging, create a Decrypted Result Beam, that can be received in the target area. In further aspects of the present invention, two or more converging waves are used to isolate one or more media components, within a multi-layered array of information storage media components, for a read or write event.

In other aspects of the invention, collateral structures and areas are protected by intentional electromagnetic interference from the opposing side of the target, causing a substantial proportion of standing waves in the electromagnetic field of the healthy tissue. This protective opposing electromagnetic interference may also be used to redirect leaked or Emerging-Slit radiation emerging from between a source and collimators and a target or related structure. In other aspects of the present invention, which may be combined with the previous aspects, by using tumor-size and healthy tissue-size related pulses, some damage directly from the ionizing beam is prevented in healthy tissue. In yet other aspects, the polarization of beams entering a target, and/or healthy collateral material, are altered relative to one another while the beams are sufficiently separated or isolatable by location of creation and direction of propagation to allow for a magnetic field to alter their relative polarizations at areas or points of superposition, to bring them into the same polarization and lead to building interference in a target, and thereby protecting collateral tissue prior to entry of the target. A reverse process with another magnetic field targeting the emergent radiation again deactivates their interference upon exiting the target. In other aspects of the invention, such a manipulable magnetic field system permits guiding particle therapy around key collateral tissues and into targets.

Aspects of the present invention are mediated by image-guiding and computational and executing hardware, which may implement real-time feedback, and independent modulation of sources, in response to such feedback in order to maximize the impact of radiation on a target, and maximize the protective effect on collateral structures.

Unless otherwise indicated, the following terms have the specific meaning described herein:

"Emergent-Slit Radiation": "Emergent-Slit Radiation," in addition to its ordinary meaning, means any energy waves that tend to emerge on one side of an opening or space between neighboring objects, due to energy transfer on the other side of the opening or space.

"Treatment Side": The "Treatment Side" of a system refers to system components that are designed, configured or intended for use in Treatment, and not used for Protection alone.

"Protection Side" (or "Protective Side"): The "Protective Side" of a system refers to system components that are designed, configured or intended for use in Protection, and not used for Treatment alone.

"Fringe Radiation" (or "Leaked Radiation"): "Fringe Radiation" or "Leaked Radiation," in addition to its ordinary meaning, refers to the unintended or undesired deviation of electromagnetic radiation or other wave-based energy transferring phenomena from a designated direction or path set forth for Treatment and includes, but is not limited to, such deviation resulting from the tendency of electromagnetic radiation to spread. Generally speaking, because radiation may be in the form of a beam of particles (which are known to contain wave as well as particle characteristics when in relative motion to an observer) as well or instead of typical electromagnetic radiation (such as gamma rays), when a statement in this application refers to radiation generally, it also should be read as a separate alternative statement referring to moving particle beam radiation, as well as the separate original textual statement, which still should be read in its ordinary sense, without the alternative statement, and each statement should be read separately from one another in the context of other surrounding statements.

"Encrypted Source Beam": "Encrypted Source Beam," in addition to its ordinary meaning, refers to an information-carrying wave (preferably, resulting from the modulation of a carrier wave) that contains only part of the information of a Decrypted Result Beam and that, when combined with another Encrypted Source Beam, superposes to form a Decrypted Result Beam at a receiving region, location or area.

"Decrypted Result Beam": "Decrypted Result Beam," in addition to its ordinary meaning, refers to an information-carrying wave that results from the superposition of two or more Encrypted Source Beams at a receiving region, location or area.

"Treatment" or "Treat": In addition to its ordinary meaning, "Treatment" means any intended affect of using any wave-based phenomenon, controlled or manipulated by a system or user, on matter or the space, point(s) or region(s) the matter occupies and/or surrounding the matter, or co-locatable with it (any of which may be called a treatment "target"), including, but not limited to, the phenomenon of ionization of living tissues by ionizing electromagnetic radiation, or heating matter with radiation, or creating superposed waves of electromagnetic radiation in such matter, space, points or regions.

"Protection" or "Protect": In addition to its ordinary meaning, "Protection" means any intended affect of using any wave-based phenomenon, controlled or manipulated by a system or user, on matter or the space, point(s) or region(s) the matter occupies and/or surrounding the matter, or co-locatable with it, to attenuate or otherwise reduce an effect of Treatment, including, but not limited to, creating a standing wave by superposing waves from opposing directions, resulting in no net energy transfer between two wave sources.

"Constructively-related Polarity": In addition to the phrase's ordinary meaning, "Constructively-related Polarity" refers to two or more waves with a polarity such that, when the two or more waves converge, superpose optimally by maintaining or increasing the nature of their polarity. For example, two plane-polarized with the same plane polarization have a constructively-related polarity. Two waves with the same chiral polarity also have a constructively-related polarity.

"Beam": In addition to its ordinary meaning, "Beam" means a wave, particle or group of waves or particles, originating from a common source, and which wave, particle or group of waves or particles, may, or may not travel parallel to or otherwise with a given fixed geometric relationship to other waves, particles or groups of waves or particles over time. For example, waves or particles within a beam may converge or diverge from one another, rather than simply run parallel to one another, depending on the focal and dispersion characteristics of the source.

DETAILED DESCRIPTION OF THE INVENTION

Figure 1:
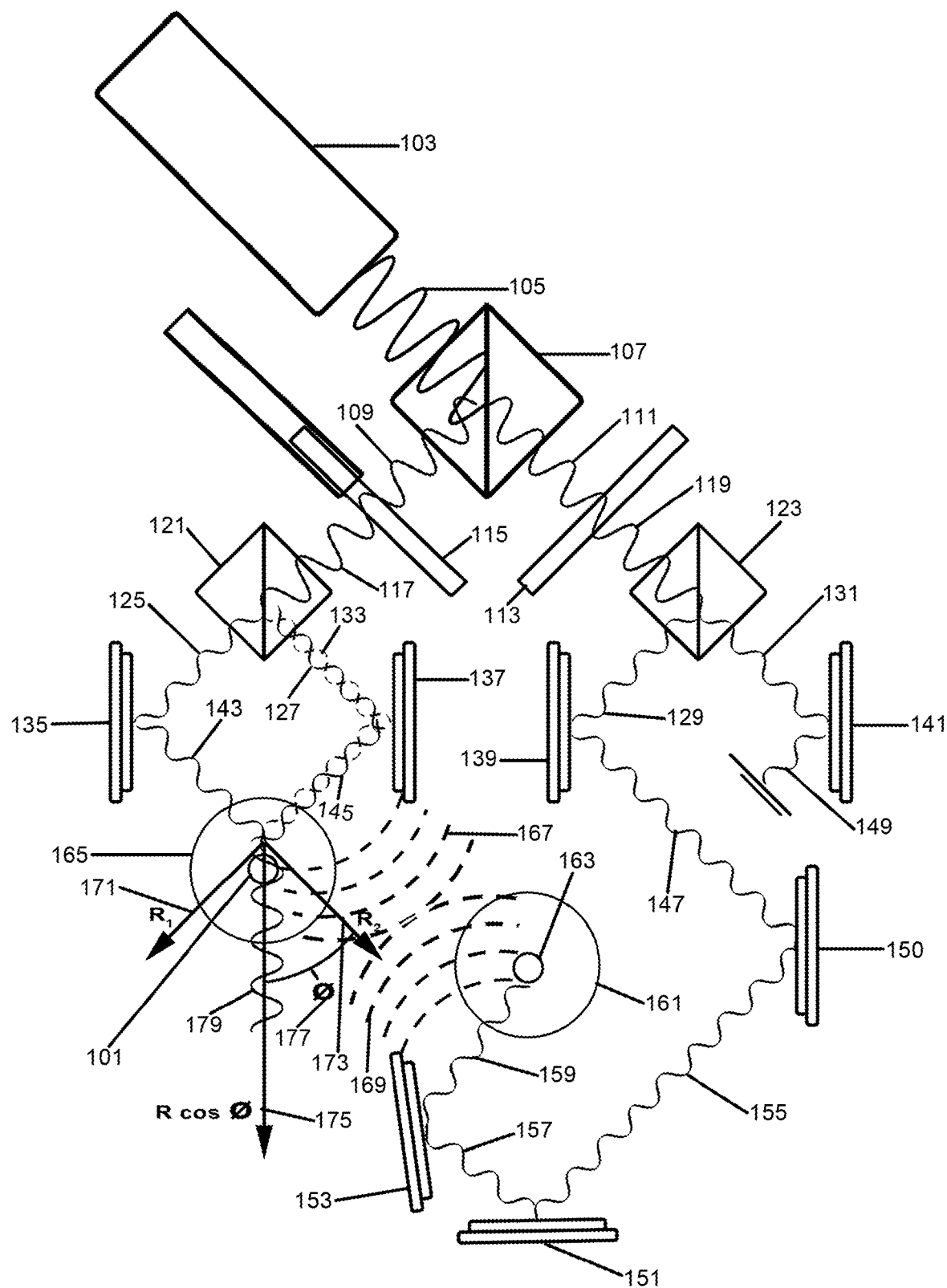
FIG. 1 is a side-view of an exemplary hardware system, and associated radiation delivery techniques, according to aspects of the present invention.

FIG. 1 illustrates a preferred embodiment of aspects of the present invention related to the delivery of enhanced electromagnetic radiation to a target, such as a tumor embedded in the healthy tissue of a medical patient. The location of the exemplary target, in FIG. 1, is shown by a cross-sectional side view through a central plane, as a spherical structure, target 101. In the upper-left corner, by the same view, an originating source 103, of electromagnetic radiation, is pictured. This source may take a variety of shapes, forms and configurations which may be suitable for creating, defining and releasing a source of electromagnetic or particle radiation, such as those used in LINAC machines. A sine wave emanating from the lower right side of originating source 103 depicts an initial radiation emission 105. Initial radiation emission 105 may be of any form of radiation with wave characteristics, but, preferably is tissue-penetrating and ionizing radiation, such as X-rays or gamma rays, in a Treatment-appropriate intensity and duration. Preferably, emission 105 is of a fixed frequency and polarity (and, even more preferably, of a chiral, circular polarization), which may be caused either by the actuating mechanism (e.g., frequency determining bombardment of a foil with particles) of the emitting appliance and/or a polarizing medium and/or filter (not pictured). Preferably, the frequency, polarity and intensity of the emission may be manipulated by the user and/or system with additional hardware and, optionally, software (not pictured). Radiation emission 105 propagates toward the lower-right corner of the figure at a 45-degree angle and next enters a beam splitter 107. After entering beam splitter 107, substantially one-half of radiation emission 105 is reflected (reflected emission 109) at a 45-degree angle, to the lower-left corner of the figure, while the other substantially one-half of the radiation (pass-through emission 111) carries directly through the beam splitter, in the original direction of propagation of beam 105. Pass-through emission 111 next passes through an optional modulator 113, which, preferably with a user interface and/or computational system (not pictured), permits the alteration of the intensity, phase, frequency and/or polarization of pass-through emission 111. At the same time, reflected emission 109 next enters modulator/blocker 115. As with modulator 113, modulator/blocker 115 permits the alteration of the intensity, phase, frequency or polarization of its emergent radiation stream 117. However, it should also be noted that the phase of reflected emission 109 may be varied by a choice of beam splitter as well. For example, if a higher refractive index material on the right-hand side of beam splitter 107 is used, reflected emission 109 will automatically have a phase 180 degrees opposing the initial radiation emission 105. Such phase reversal is desired in aspects of the present invention, for reasons which will be explained, below.

Emergent radiation beams 117 and 119 next enter beam splitters 121 and 123, respectively, yielding emergent beams 125, 127, 129 and 131. It should be noted that, in another embodiment, beams 125 through 131 could themselves enter additional modulators, actuated by a control system. However, preferably, they are not modulated at this point in the stream of events. Potentially-created emergent beam 133 preferably is not created by the system but is depicted to illustrate the 180-degree reverse phase that might emerge if a different coupling of refractive materials is used in beam splitter 121, with different relative refractive indices. Next, emergent beams 125 through 131 reflect against mirrors 135 through 141, creating emergent beams 143 through 149.

At this point, it is useful to refer to emergent beams 143 and 145 as being within a class of system components termed the "Treatment Side" of the system. The Treatment Side serves to deliver ionizing or otherwise target-affecting radiation to a target. Meanwhile, emergent beams 147 and 149 may be described as being within the "Protective Side" of the system. The Protective Side serves to moderate or reduce the net force or affect of radiation emerging from the Treatment Side in areas where such moderation or "Protection" is desired. The Treatment Side and Protective Side components are described further in FIG. 2. In the instance depicted in FIG. 1, it may be assumed to be desired to affect target 101 with ionizing radiation. Thus, beams 143 and 145 converge upon the target and, preferably and as will be explained further, below, with a greater amount of their radiation beams focused on and converging on the leading portions (facing the beams) (a.k.a. "proximal" to the beams) than on the distal portions of the target. However, beams 147 and 149 (the latter of which is only partially pictured, for 2-D illustration purposes) pass through a series of mirrors, including pictured mirrors 150 through 153, resulting in an emergent beam 159 hitting a diffusing media and complementary target clone 161 and 163. The size, angles, orientation and refractive indices of the diffusing media and complementary target 161 and 163 are selected to match or approximate those of the actual target 101 and collateral material 165, such that any emerging radiation 167 is matched by emerging radiation from an opposing angle 169, which is, owing to the distances and angles of components chosen by the system and/or user, matched in phase with emerging radiation 167. As a result, a portion of emerging radiation 167 is superposed through interference with emerging radiation 169, creating standing waves, which do not transfer ionizing energy.

Turning again to radiation waves in beams 143 and 145, converging on the leading volume of target 101, the system has caused the radiation wave in beam 143 to be in-phase, identically polarized and to have the same frequency and, preferably, the same energy and amplitude. Therefore, as the beams converge, they superpose and interfere—substantially increasing in power, Kerma and Joules per kilogram of Treated matter in the areas of convergence and superposition. In general, assuming that the two converging radiation beams are of identical energy, they will vector sum as they converge, according to the formula 2R cos Ø, in which R is a measure of the energy level or strength of each of the adding source beams, shown as vectors 171 and 173, and Ø is the angle between each of the source beams and the resulting beam vector 175, which angle Ø is shown as 177 in FIG. 1. Where, as in the example angles shown in FIG. 1, the angle Ø is 45 degrees, the resulting vector sum 175 and beam 179 is therefore approximately 71% of the strength of the scalar sum of the two beams, as a result of the vector sum.

The angle Ø may be made more acute or oblique, and, generally, will have greater definition between a Treatment target and collateral tissue in the latter instance, but have a greater maximum power differential in the former instance. It should be noted that the particular types of radiation reflecting, modulating, focusing and diffusing devices pictured in FIG. 1 are illustrative, but not exhaustive. The particular angles, distances of the radiation propagations, beam splitters, mirrors and other optical devices may be of any suitable choice for reflecting, splitting, delaying or otherwise altering the directions, distances and other aspects of electromagnetic radiation, or otherwise carrying out aspects of the invention. For example, a dual-prism square beam splitter need not be the type of beam splitter used, and the emergent collateral radiation may be accomplished to some degree with a diffusing lens, rather than a complementary opening. Radiation may be amplified at any point or in any area, for example, by optical amplification in a medium (not pictured) or the amounts directed to each beam may be attenuated with amplification of a source beam (or source beams), to correct or optimize the distribution of radiation and allow for constructive and destructive interference of the correct vectors to optimize Protection and Treatment according to aspects of the present invention. Furthermore, it should be understood that many other methods may be used to generate complementary, inverse waves such as those created by the system depicted in FIG. 1, and the present invention is in no way limited to the exact techniques explained with respect to FIG. 1. For example, multiple emitters may be used and separately controlled and modulated through feedback to yield such interference, rather than splitting an originating beam. However, splitting an originating beam may have some advantages, as well as drawbacks, over other approaches to carry out aspects of the present invention. It is also possible to drive, create, simulate or amplify attenuating Protective radiation (or anti-radiation), for example, by magnetic or electromagnetic amplification or attenuation transmitted or pulsed from the same side as the Treatment beam, and/or from the opposing side, (or vice versa, with respect to the Protection Side), rendering it out-of-phase, causing more attenuated, and otherwise different ionization or other radiation effects in desired areas of Protection coverage.

Figure 2:
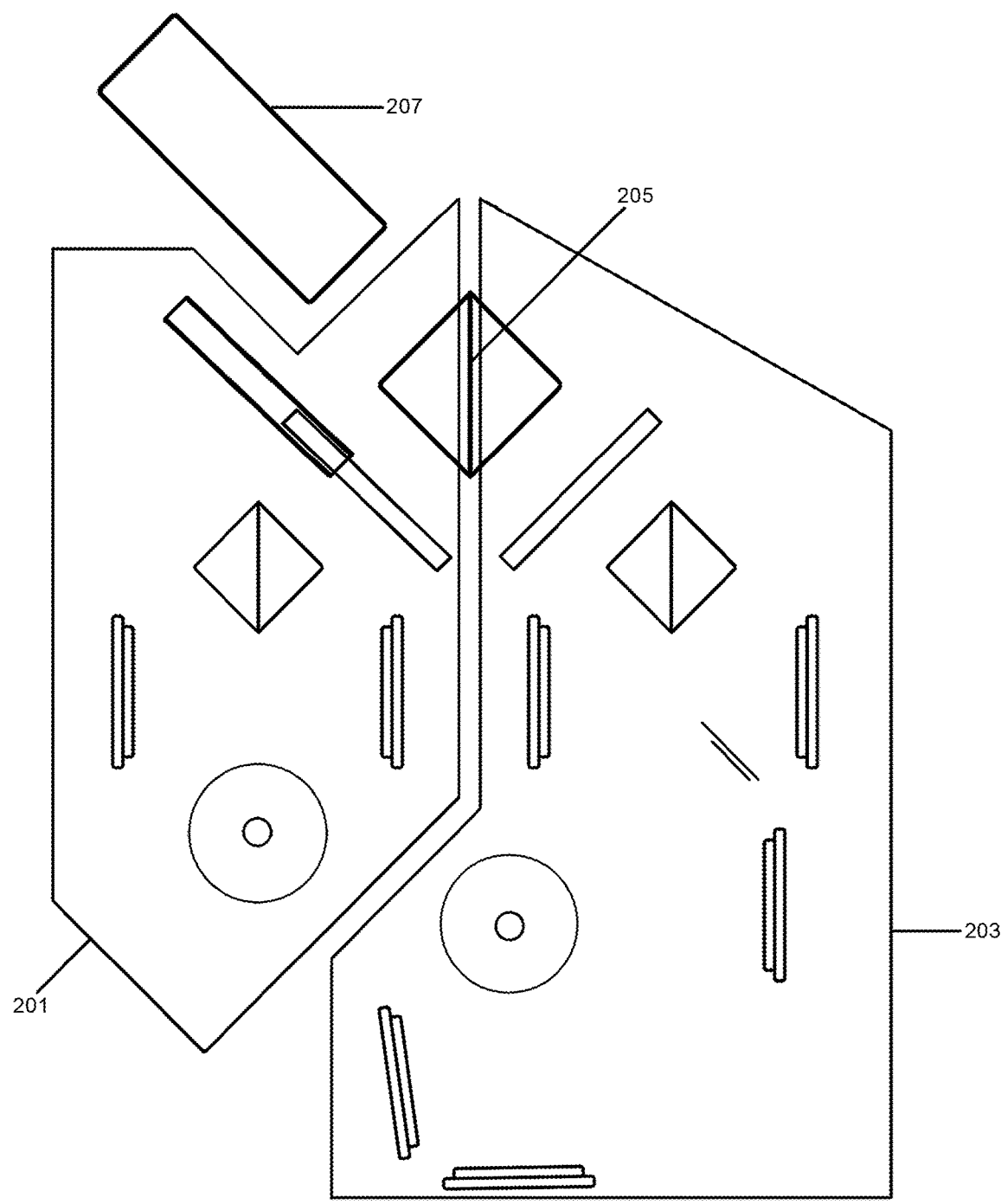
FIG. 2 depicts the same exemplary hardware system as in FIG. 1, further depicting which system components are either in the "Treatment Side" or "Protective Side" of the system.

As alluded to above, FIG. 2 aids in explaining which of the components of the exemplary system depicted in FIG. 1 are within the Treatment Side or Protective Side of the system. All components within the box encompassing Treatment Side components—box 201—can be thought of as a part of the Treatment Side of the system. All components within the box encompassing Protective Side components—box 203—can be thought of as a part of the Protective Side of the system. Components contributing, but not entirely within either the Protective Side or Treatment Side of the system, as shown in FIG. 2, include the originating source, shown as 207 in FIG. 2, and first beam splitter in the beam sequence, shown as 205, which may be thought of as present in both system sides.

Figure 3:
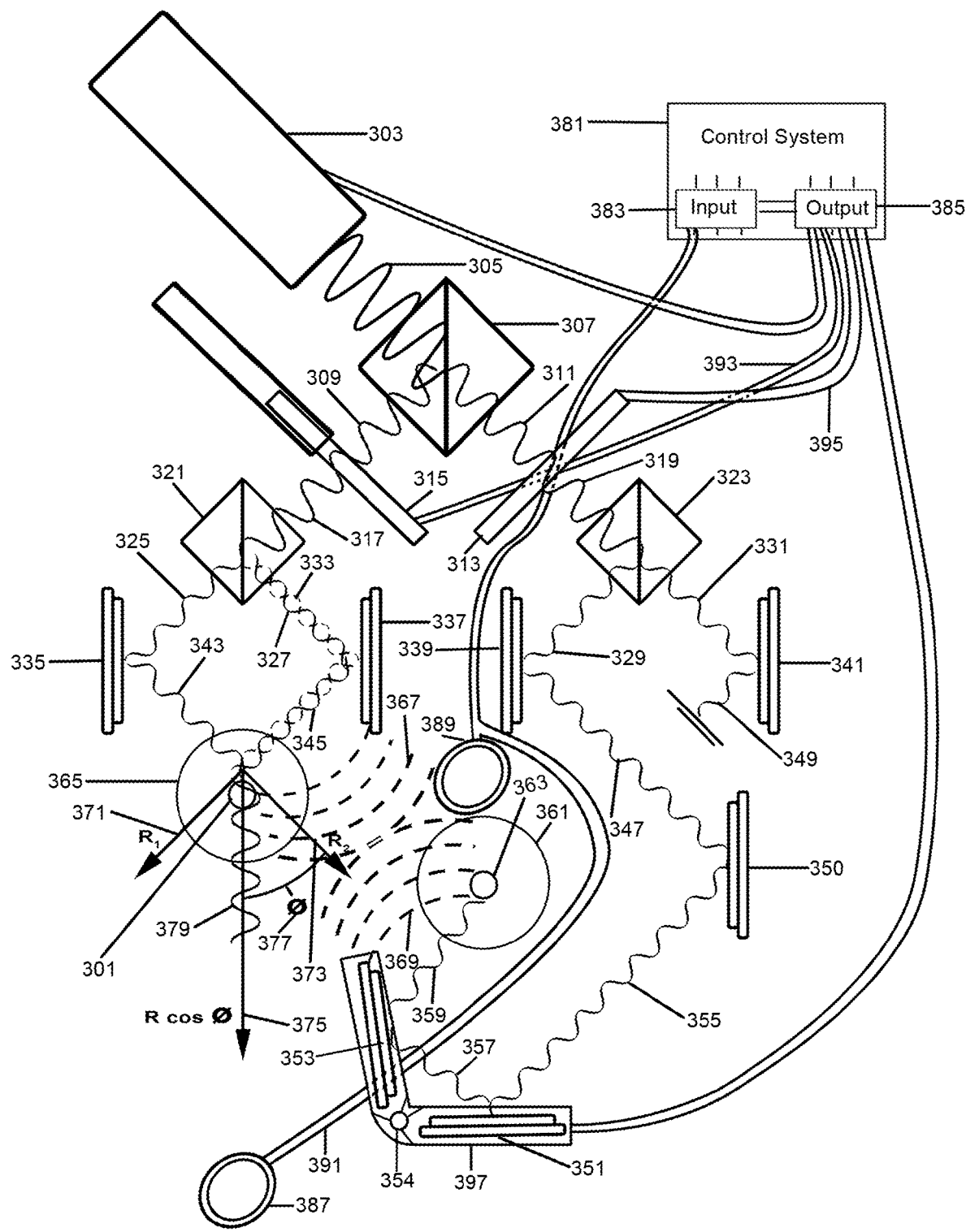
FIG. 3 depicts the exemplary hardware system of FIG. 1, further explicated to include sensory and feedback hardware and techniques in relation thereto.

FIG. 3 depicts the same system discussed in FIGS. 1 and 2, with additional control hardware and techniques depicted. A control system 381 appears in the upper-right corner of the figure, and may include input 383 and output 385 devices and their connectors and circuitry, which allow the control system to give and receive signals, instructions and information to and from sensors 387 and 389. Sensor 387 is located within the path of the stream of resulting vector beam 379, and may sense, among other characteristics, the strength, period, phase, frequency, and amplitude or energy of ambient and/or directional radiation. Sensor 387 passes a signal with any or all of that sensory information by transmission wires/bus 391. Of course, transmission may be by any suitable means, such as RF signal circuitry and hardware, as well as the pictured hard wiring, but hard wiring is preferred in order to avoid unintentional interference with other aspects of the invention. Sensor 389 also permits the system to sense radiation and any of its sensible characteristics, but, in this instance, is located near the convergence of the leaked Emergent-Slit Radiation 367 and Protective radiation 369. Based on information received by the system, the system may modulate and tune radiation on both the Treatment Side and the Protective Side of the hardware system with output signals or instructions carried on leads 393 and 395, to modulator 313 and modulator/blocker 315. For example, if sensor 389 detects that the Protective radiation 369 is not interfering properly or completely enough, for example, because the resulting wave form is not in a well-defined single standing wave phase, the system may, for example, adjust the energy level, amplitude, phase or polarization of source radiation beam 317, using modulator 315, until the leaked radiation and Protective radiation are sensed to properly interfere more completely. Additional sensors (not pictured), including sensors for beams 343 and 345, might also pass characteristics information regarding any beam, including, but not limited to, the individual source beams contributing to resulting vector beam 379, and allow the system to tune those characteristics using modulators of each of those streams (not pictured) individually. Control system 381 may also be used to control spatial configuration actuators or servos for any system component, including, but not limited to, 3-dimensional pivot and scissoring device 397, which may re-orient mirrors 351 and 353 in space—in part, by actuating motorized hinge 354. The distance and orientation of mirrors 351 and 353, and any other individual device or hardware item in the system of FIG. 3 may be further altered with respect to the target 301 and additional system hardware, such as mirror 350, via telescoping and rotating actuators or servos and/or by mounting other variable component-connecting hardware—for example, a telescoping and rotating servo and hardware between mirror array 351/353 and mirror 350, or an adjustable fixative bracket between mirror 353 and target and collateral clone 363 and 361. In this way, the control system may adjust hardware to fit targets of varying size and location efficiently and conveniently, and may also adjust the 3-D orientation of hardware to maximize the effectiveness and efficiency of both the Treatment Side and Protective Side of the system, for example, to tune source beams 343, 345 and 359 in light of refraction effects or live information attributed to or resulting from the target 301 and collateral Protected material 365. For example, MRI sensory and imaging information may be taken of the target 301 and collateral Protected material 365 on a live basis through MRI hardware (not pictured) and sent to the control system via leads (not pictured) to input 385. Based on radiation refractive property models held in, or accessible to, control system 381, a refractive profile for the target 301 and collateral Protected material 365 may be built, and actual and anticipated radiation from any point around or within the target 301 and collateral Protected material 365 may be compared to data projected by those models. For example, a model such as the MIRD-5 phantom computational body model developed by the Oak Ridge National Laboratory, may be used as a platform and modified by the system, including organ surface refraction, fluorescence and scattering effects. In the event of substantial, sustained deviation from anticipated or projected and actual radiation measurements, adjustments to the refraction models and actuated or controlled system hardware may be made that explain and/or compensate for the deviation. In addition, hardware 3-D orientations and beam characteristics may be adjusted to further compensate for such unexpected, newly learned refractive profile characteristics, thereby optimizing system performance. In addition, the system may exploit natural lensing effects that take place in collateral tissue, to allow diffuse radiation across broader, lensing collateral material to focus radiation on a target volume.

Additional Treatment and Protective sources, and/or such sources of greater complexity, with, for example, more radiation source beam origination points, may be introduced into the system to address more complex refraction phenomena profiled than that pictured in FIGS. 1 through 3, and to address target, collateral material or other subject- or media-related reflection, blocking and refraction effects.

Figure 19:
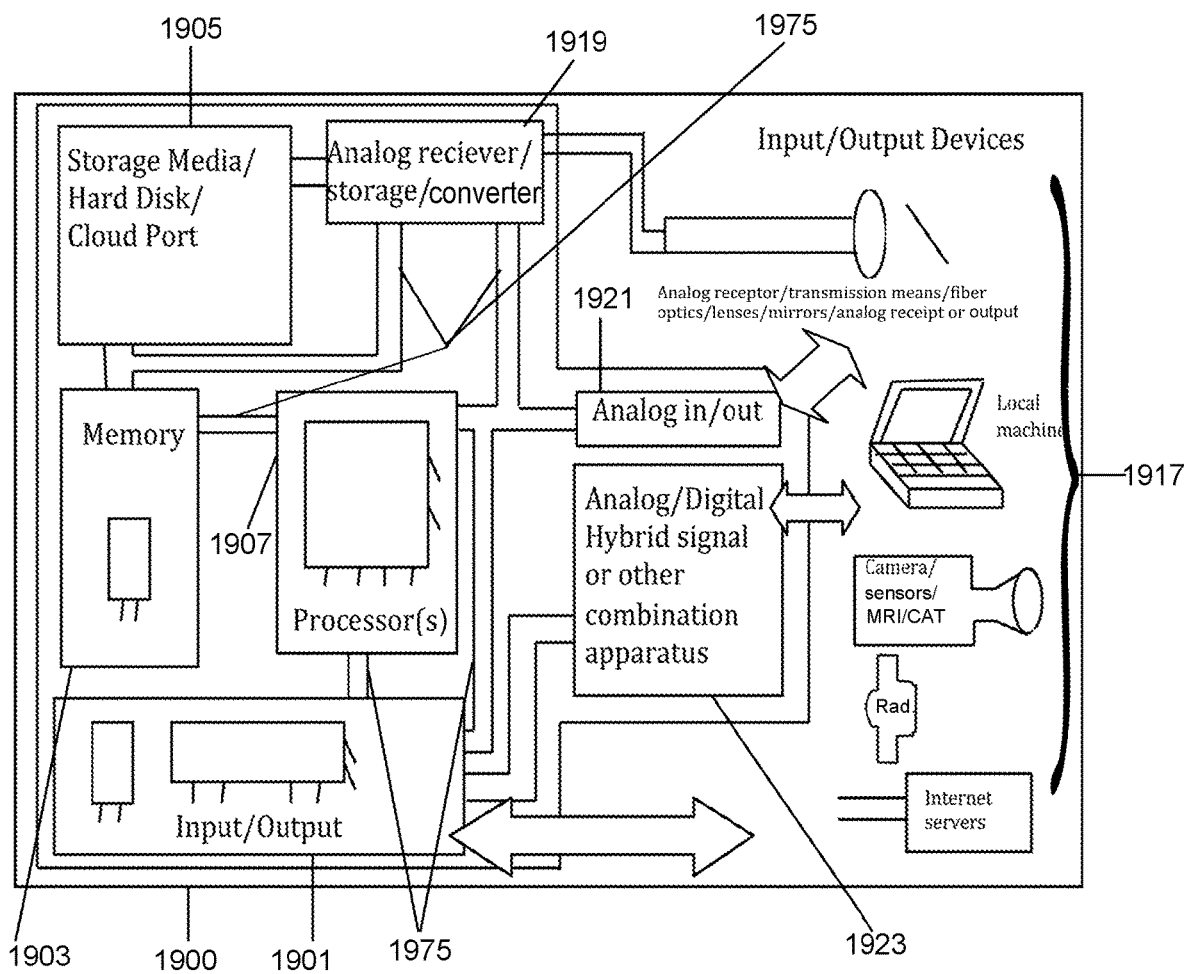
FIG. 19 is a block diagram of some elements of a control system that may be used to implement various aspects of the present invention, other elements of which are depicted in, and discussed in relation to, FIGS. 1-18.

A control system, which may supplement or replace 381, including some of its user interface options, is described in greater detail in FIG. 19.

To reduce loss of radiation from conversion of a multi-directional source to a source beam, anamorphic mirror and/or lensing, or holographic techniques, may alternatively be used to recreate a reversed image of the source, or part thereof, in the target volume, as an alternative to the mirror array described in FIGS. 1-3.

Figure 4:
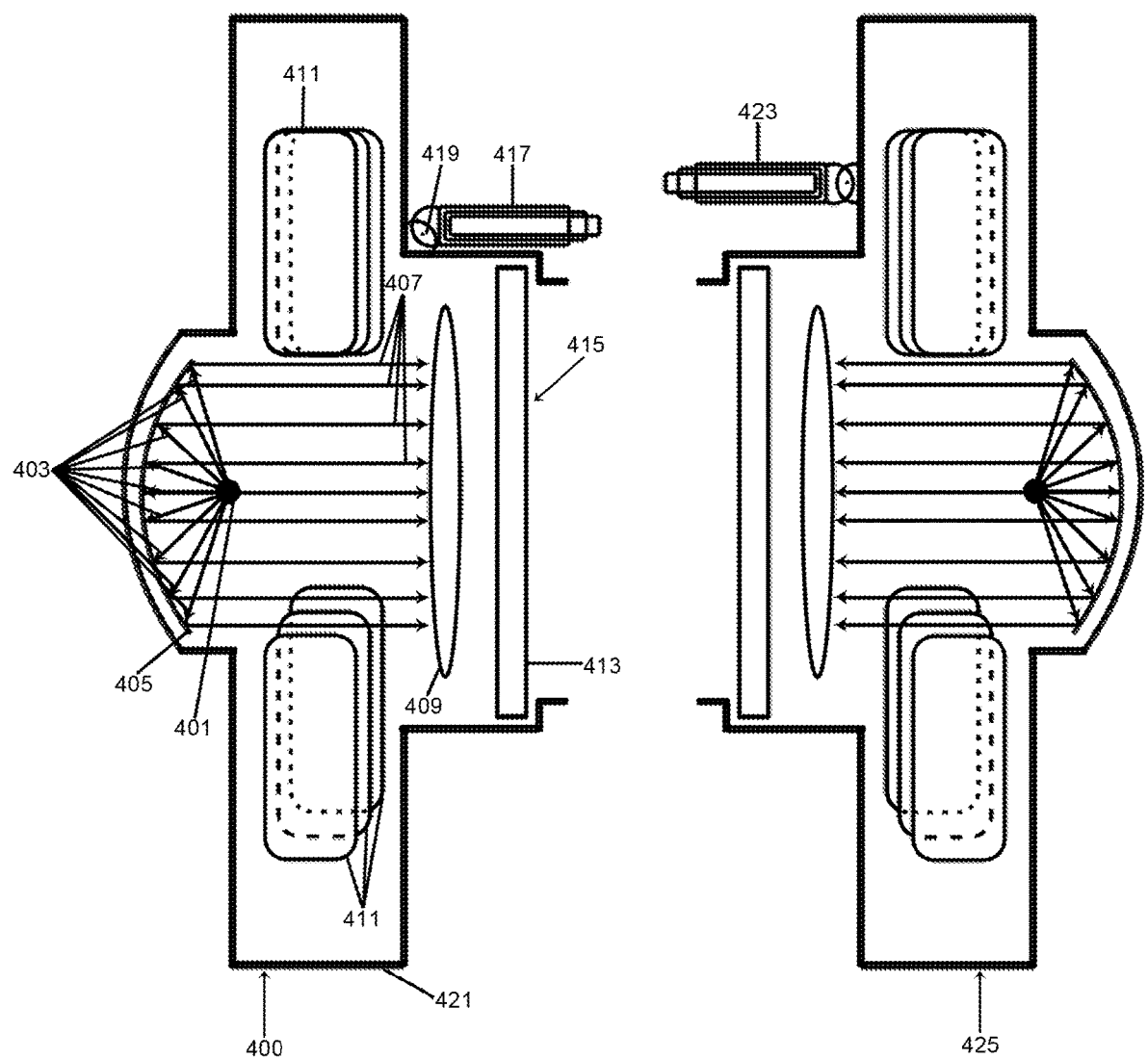
FIG. 4 depicts hardware that may comprise and control a source of radiation, in accordance with aspects of the present invention.

FIG. 4 depicts beam collimating, source orientation and other structural and controlling hardware which may comprise or control radiation sources in accordance with aspects of the present invention. Unlike with FIGS. 1-3, the common origination and splitting and reflection of a source beam for multiple sources is not pictured. However, it should be understood that any source pictured in FIG. 4, and in other related figures including a radiation source, may be commonly derived from such a master source, as described in FIGS. 1-3. Beginning with source 400, radiation is initially emitted in several directions, exemplified by ray paths 403. Those ray paths hit a substantially parabolic mirror or reflector/absorber 405. Because the source radiation origination point 401 is located at the focus point of the parabolic shape of 405, this leads reflected efferent radiation rays 407 to approach lens element 409 in substantially parallel pathways. However, owing to the natural incoherence and expansion of the plane waves of electromagnetic radiation and otherwise errant particle radiation, collimators, such as multi-leaf collimators 411, may be used to shape and restrict the total beam of radiation that will enter lens element 409 and, ultimately, exit the hardware after being focused and/or diffused by lens element 409. Collimators 411, and lens element 409, may be real-time 3-D conformational, tailoring the beam's shape according to MRI or other imaging and sensory feedback and refraction models, as further explained with respect to other aspects of the present invention.

Rather than a conventional lens, lens element 409 may be replaced by a new form of lens element better equipped to handle the wear and tear of focusing higher-energy radiation. For example, a lens element with replaceable lens-shaped compartment-bounding elements, and an interstitial refractive and/or cooling fluid, which may circulate in and out of an external chamber(s), such as a bladder or tank, and lead channels, via a pump, to avoid overheating and breakdown, may be added. In addition, the lens-shaped compartment bounding elements may bound just the radiation entry and exit sides of the lens element, and may slide, while still sealing the interstitial fluid from leakage, along at least one side-walling element, which need not be transparent or translucent. As the lens-shaped compartment-bounding elements expand or contract together, they may change their shape to have more or less acute gradations, and different focal effects, by a graduated elastic aspect along their expanse, radiating from their center, and the central chamber may naturally draw in more or less fluid, as a vacuum or positive pressure is built, above the pressure naturally created by the circulation system. The focus may also be changed by electrically-actuated or magnetically-actuated control points on the lens-shaped elements (or magnetically-actuated and orienting elements in the fluid, which change their refractive properties in different magnetically-actuated orientations in space), and may be so numerous as to allow effectively unlimited conformational changes in the lens shape.

As explained with reference to FIG. 19, below, a control system may instantaneously test 3-D orientation of source or hardware movements or focal lengths and areas and radiation characteristic changes in multiple ways, evaluate improvement or deterioration of Treatment and Protective radiation interference and radiation delivery, such as by test instances, and implement changes according to that feedback. Thereafter, the system may implement further tuning based on additional instantaneous testing and comparison to the results of the previous orientation and beam characteristics to assess improvement. If no overall improvement has been made, the system may revert to the previous orientation and beam characteristics. Among other things, such modulation and focusing of the radiation source may better address target and collateral matter movement, including movements between target and collateral matter. Lens element 409 may either focus or diffuse efferent radiation, depending upon the needs of the system. Lens element 409 may be a single lens, or a complex of lenses and/or parabolic mirror 405 may itself not be perfectly parabolic, with an integrated or derived angle deformation adjustment that diffuses and/or focuses efferent radiation relatively uniformly, or in conformity with a desired Treatment area dosage distribution. For example, the function for the parabola may be modified to result in a unit-by-unit adjustment (e.g., subtract 0.01 millimeters from the x-axis for each function output per millimeter along the y-axis, to cause uniform diffusion or focusing). Such a function might thereby be described as $f(y)=(x-0.01y)^2$, for example. Such a pseudo-parabolic mirror could obviate the lens element 409, which may be omitted. After passing through lens element 409, the efferent radiation may enter a polarizing and/or modulating filter or filter blocker 413. Element 413 may permit the source to restrict radiation to one phase, one polarity and one frequency and/or intensity, or a range or ranges thereof, among other characteristics, or a stream, succession or grouping of instances of such characteristics, as may be needed by the system to optimize performance due to interference with other sources and the refraction blocking and reflection characteristics of the target, medium and collateral material of a subject and Protective Radiation, if any. Appropriate radiation emission, or patterns thereof, then exit the source at port 415. To reduce the risk of leaking radiation, blocking element 417, variably attached (e.g., by a detachable and conformable ball-and-socket joint 419) to the source housing 421, may be used, which is preferably made of a material or structure or force field that substantially absorbs stray or Fringe Radiation from the source, out-of-line with an intended beam path. Element 417 is preferably a telescoping member comprising matter of high radiation absorptiveness, such as lead, such that different distances between sources, targets, collateral material and media may be physically accommodated. In Treatment configurations with multiple sources, the positioning of blocking members, such as that illustrated as 423 attached to a paired source, 425. Such accommodating configurations allow for gapless interlocking of the blocking elements, even if telescoped, to prevent or limit stray or unintended peripheral radiation. A literal locking mechanism, such as flexible unisex or multi- or omni-valent latching or other reversible physical binding on every surface of every blocker, which may close any gap between neighboring blocking elements on multiple sources, is preferred.

Figure 5:
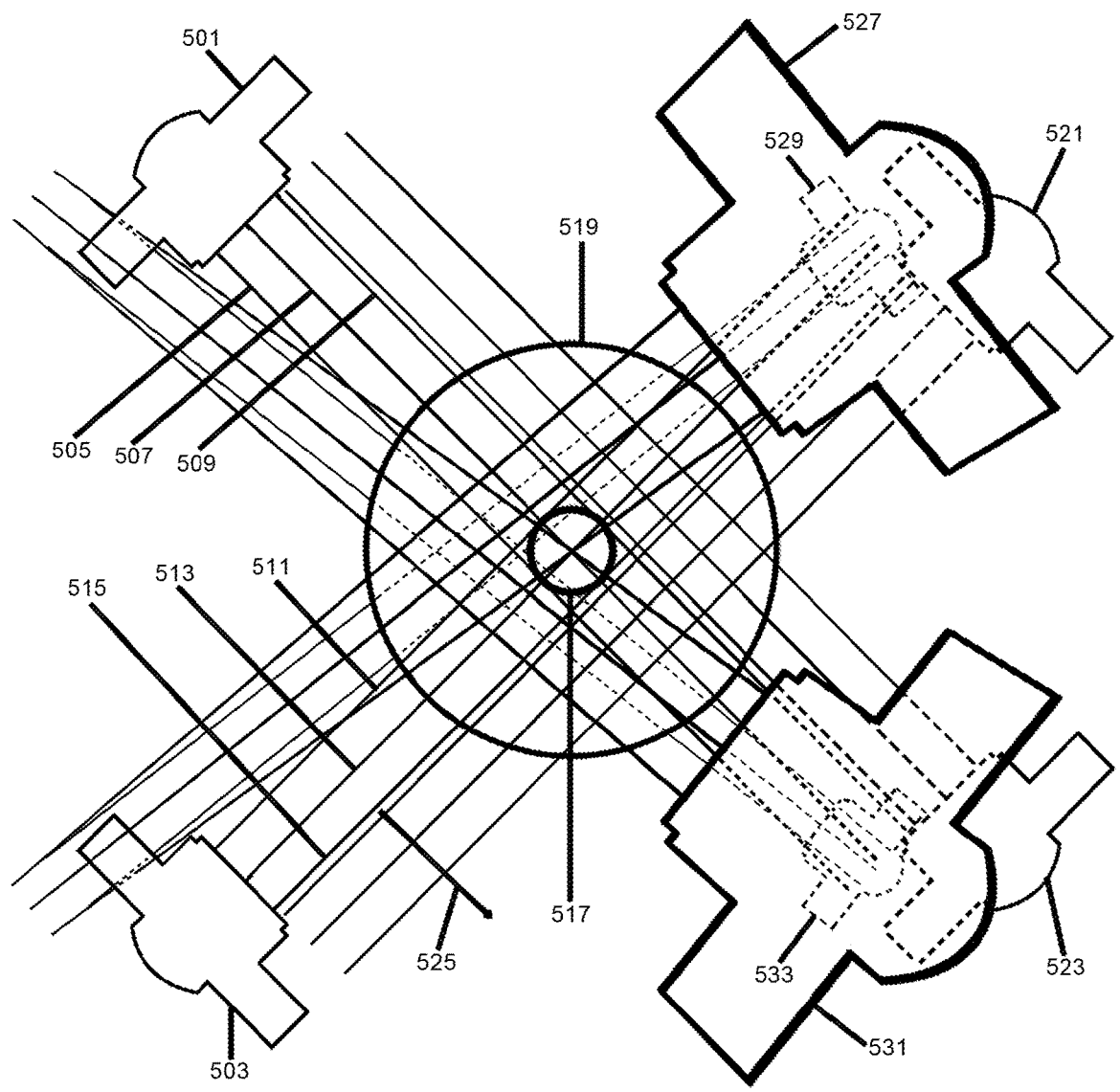
FIG. 5 depicts another exemplary hardware system and associated radiation delivery techniques, with multiple sources such as those depicted in FIG. 4, which may be used to carry out aspects of the present invention.

FIG. 5 depicts another exemplary hardware system and associated radiation delivery system and techniques, with multiple sources such as those depicted in FIGS. 1-4, which may be used to carry out aspects of the present invention. Treatment-side sources 501 and 503 emit radiation generally from the left-hand side of the figure toward the right-hand side and, more specifically, in the direction indicated by beam lines 505 through 515. More particularly, the beam of radiation emitted from source 501 is directed toward the lower-right corner of the figure while the beam of radiation emitted from source 503 is directed toward the upper-right corner of the figure. By techniques and mechanisms discussed elsewhere in this application, as above, in connection with FIG. 4, the radiation from sources 501 and 503 is preferably in the same phase, of the same or a complementarily superposing polarity (and even more preferably, of a matching chiral pair of polarizations), and the same frequency and intensity, or any one of those characteristics, but, preferably, each of those characteristics. Thus, as discussed earlier in this application, as the cross-sections of the beams of radiation from sources 501 and 503 converge, near or about the volume of a target mass 517, the radiation vectors sum to resultant superposed beam of greater magnitude and/or a greater or otherwise desired superposition-resulting frequency, or other desired superposition combination, depending on the angle separating the direction of the two sources 501 and 503, and their beams, whose direction are shown by rays 505 through 509 and 511 through 515, respectively, and also depending on the magnitude of those Treatment-Side beams. Also by mechanisms and techniques described elsewhere in this application, complementary Protective-Side radiation sources 521 and 523 introduce superposing radiation (preferably of the same frequency, intensity and of appropriate polarity such that it interferes inversely with radiation emanating from Treatment-Side sources (propagating in an at least partially opposing direction in a matching amount in that direction), such as plane wave radiation expanding beyond directional rays 505 through 515). In this way, sources 521 and 523 have the net effect of compressing and trimming the effect of fringe or "leaked" radiation expanding beyond the desired Treatment and/or communication target 517, by greatly reducing the transfer of energy by the Treatment-Side sources to collateral material 519. Accordingly, sources 521 and 523 may be thought of as Protective-Side components and, more specifically, as Protecting collateral material from fringe radiation on the outer edges of the sources. It should be noted that, in this configuration, Protective outer edge radiation sources 521 and 523 are powered at lower level than their paired Treatment sources 501 and 503, respectively. More preferably, Protective sources 521 and 523 are outfitted with partially-absorptive filters (not pictured) that reduce the intensity and/or density of the interfering Protective radiation beam if one were to assess the resulting beam/field of Protective radiation moving from directional rays at the edge of the Protective beam nearest the Treatment beam and moving one's assessment toward the outer edge of those directional rays, by, for example, an assessment sensor passed approximately through a plan bisecting such a beam, the direction of such an assessment path being that shown by arrow 525. The exact power levels and attrition of the beams laterally or vertically in any rotation orientation of the source, and across any localized plane or volume, may be modulated by an actuated filter and control system (not pictured), and may be adjusted in real time based on sensory feedback concerning the resulting radiation field. For example, if the fringe radiation and Protective radiation are not harmonic, not interfering, not producing standing waves, or are determined to be transferring ionizing radiation that may be further reduced by modulation of either the source radiation or the Protective radiation, the control system may so modulate either the source radiation or the Protective radiation, and with each source, independently, to optimize Treatment and/or Protection given the refraction of collateral material and media, and/or real-time deviation from refractive profiles maintained and adjusted, in the control system. As mentioned previously with respect to other embodiments, instantaneous or other testing, at substantially lower dosages than the majority of the Treatment time, may be used to model and alter 3-D refraction and blocking profiles and models for the target and collateral material.

As mentioned previously, the radiation refraction and blocking profiles of targets, collateral material and other media can reduce the effectiveness of paired Treatment sources and Protective sources, which serve to concentrate ionizing radiation, or other, for example, combined signal-carrying radiation, in desired areas. In addition to modifying the intensity and other radiation characteristics emanating from sources, the control system may dictate additional or different ray paths for either the Treatment or Protective sources (and any one or group thereof) by efferent radiation dynamic actuated lenses, filters and/or modifying the number, placement and angle of Protective and Treatment sources to improve the distribution of ionizing and protective radiation, based on refractive/reflective models and live sensory feedback.

In any event, preferably, additional Protective Side sources are also used, to also address leaked or fringe radiation on the inner area, between the sides of Protective sources closest to one another. Such additional Protective sources are shown as sources 527, 529, 531 and 533 which are aimed to Protect collateral material and media from source fringe radiation from that inner area and, preferably, are aimed toward or through the central plane evenly bisecting laterally the Treatment-Side sources and target volume, but at an angle permitting the graduated distribution of Protective radiation to better match fringe radiation with an optimal avoidance of unintentional protective radiation in the target volume. Generally speaking, Protective beam paths aimed tangentially to target structures, at angles more oblique than 90 degrees with respect to the central source and target bisecting plane will be more optimized and require less Protective source power. Unlike Protective beams 521 and 523, sources 527 through 533 are preferably mounted by hardware (not shown) above and below the central plane bisecting the originating sources 501 and 503 and the Treatment target 517, such that a lower amount of Protective radiation passes through the target. Because Protective sources 527-529 are above and below that central plane, their beam paths may cross over and under the target, thereby partially Protecting fringe radiation in those areas as well, which Protective beams 521 and 523 cannot do as effectively.

It should be noted that, although it is preferred that Treatment Side sources emit electromagnetic radiation or other energy-transmitting waves of the same polarity, period and frequency, it may be preferable, in some embodiments, to use a different or more random polarity, period or frequency. For example, to create a superposed frequency that is greater (which may be advantageous for creating a different, increased electromagnetic energy level, waves of a different period, and even different frequencies, may be used. Oscillating, different frequencies, brought together, may also create patterns of increased energy, or energy spikes, that are advantageous, to destroy cells that move with a cyclical biological process (e.g., breathing, heartbeat).

Figure 6:
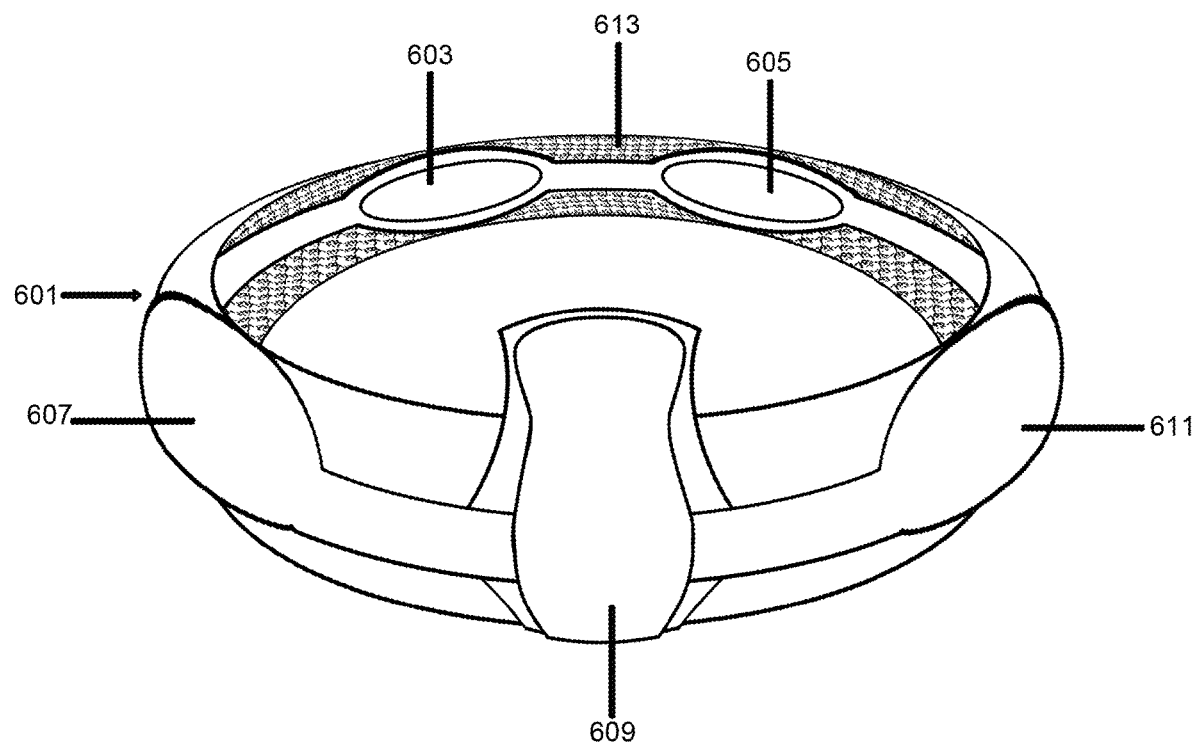
FIG. 6 is a perspective view illustration of a structural array of a complex of Protective Side and Treatment Side radiation sources, demonstrating the operation of preferred embodiments of the present invention in three-dimensional ("3-D") space.

FIG. 6 is a perspective view illustration of a device comprised of a structural array of multiple Protective Side and Treatment Side sources, demonstrating the operation of preferred embodiments of the present invention in 3-D space. Device 601 is depicted generally as a ring structure, with Treatment sources 603 and 605 generally facing a viewer of the figure, as well as the inside of the ring structure on the opposing side, preferably, focusing their efferent radiation on a target toward the center of the ring structure (e.g., a cancerous tumor target within a patient laying on a bed inserted into the ring structure). Sources 607 and 611 emit Protective radiation, according to aspects of the present invention described above, from the outer edges of beam paths from sources 603 and 605 and outward from the center of the ring, thereby reducing fringe radiation, expanding beyond the desired beam paths for sources 603 and 605. Radiation-diffusing and edged surface coating 613 may line the inner surface of the ring structure, absorbing and/or reflecting away radiation emanating from sources that has already passed through the target volume of the ring structure and hit the inner surface of the ring structure, and preventing the majority of that radiation from re-entering the collateral area surrounding a target. Although not pictured, such surface coating may cover any other structure that may create undesired reflections. In addition to diffusing edges, surface coating 613 may also have downward-facing facets, to further absorb and reflect radiation reflecting on lower, upward-facing facets of the coating.

The lenses of all sources shown in FIG. 6 are not simple spherical or parabolic shapes. Rather, they illustrate a more desirable multifunctional and/or 3-D conformational blend of shapes, leading to improved shaped radiation beams. For example, Protective source 609 extends more greatly above and below the plane bisecting ring structure 601 into two equal, uniformly-shaped rings than other sources, and as its structure reaches inward both above and below that plane, the width of the source increases. Thus, source 609 is capable of generating a greater density of radiation, from a greater distribution of angles and yet at angles that still conform with the edges of the beam paths from sources 603 and 605, despite the change in distance. Ray paths from source 609 preferably converge just beyond (viewing from the perspective of the drawing) the convergence of ray paths from the Treatment sources, thereby attenuating Fringe Radiation where it is greatest. Alternatively, the protective beam paths of source 609 may face outward from the center of the source head, by a shape or other mechanism aiming its edges along the edges of ionizing source radiation, which, itself, preferably converges on the leading volumetric features of the target. Controllable, graduated modulators or filters may adjust radiation emanating from different regions of sources. For example, source 609 may adjust phase, period, frequency, intensity, amplitude and other characteristics to maximize Protective interference across the beam profile, as it crosses leaked Fringe radiation from the Treatment sources. Other sources, by contrast, may capitalize on additional lateral space, along the ring structure, thereby becoming more ovoid, or a blend with another curved or graduated structure and the primary beam-shaping structure (e.g., parabola or decaying parabola, as discussed with respect to FIG. 4), allowing for a greater number of convergent angles, more diffused across collateral structure and media space.

In another embodiment, ring structure 601 may be split into two or more complementary beam structures, rather than one (such as the ring structure pictured), with overlapping regions coated, such as with coating 613. In such an embodiment, the ray paths may be adjustable to accommodate differing distances between the sources, as they are brought closer or further apart—for example, by flexible, uniform bending of the multiple, complementary semi-ring structures, of the sources alone or by actuation of lens or reflector controls by a control system, such as the control system discussed in connection with FIG. 19. All of the same control system and other features and aspects discussed with respect to systems depicted in FIGS. 1-5 are also possible with respect to FIG. 6.

Figure 7:
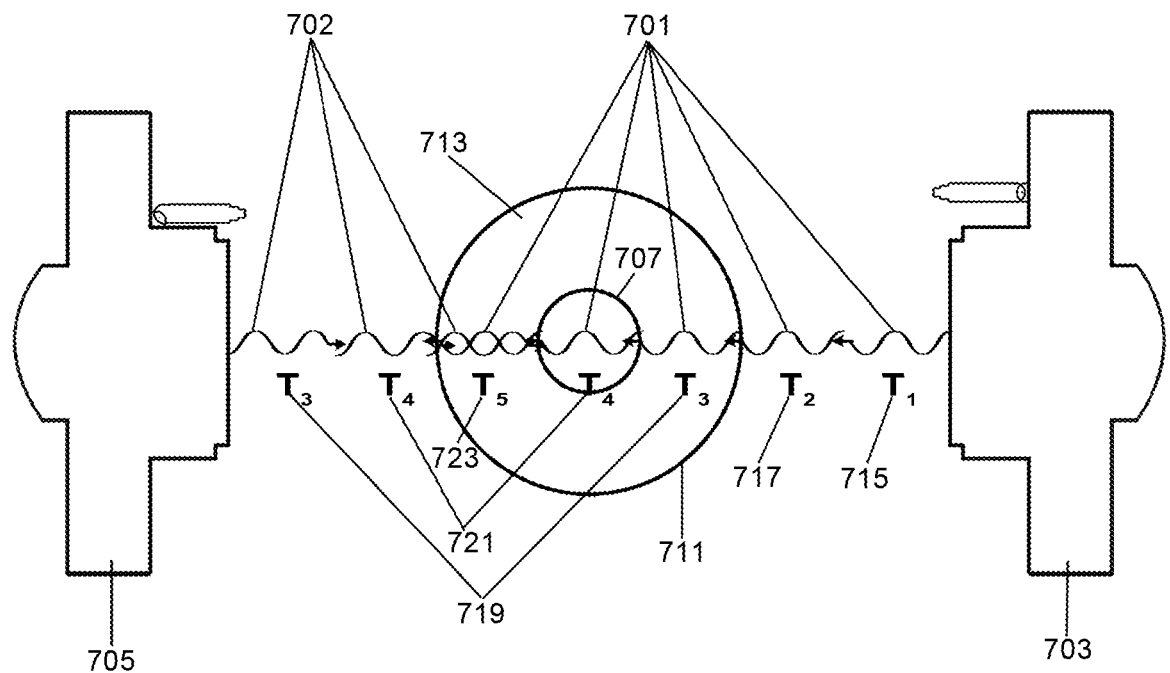
FIG. 7 is a graphical depiction of a hardware-incorporating system delivering targeted controlled-length pulses of radiation, and the timing and orientation of such pulses, according to aspects of the present invention.

FIG. 7 is a graphical depiction of radiation sources delivering targeted controlled-length pulses of radiation, according to aspects of the present invention. Sources 703 and 705 are each facing, and placed on opposing sides of, a radiation Treatment target volume 707, and its collateral volume 711. Two exemplary pulses of radiation, each a produced increased concentration of radiation of a particular width, once emitted, are depicted, if they have yet been created by a source, at instances of time indicated by point-in-time-associated time/location indicators 715, 717, 719, 721 and 723—with notations $T_1$, $T_2$, $T_3$, $T_4$, and $T_5$, respectively—which are placed directly below depictions of the location of Pulse 701 or 702, or both Pulse 701 and 702, at the instances of time indicated. Source 703, on the right-hand side of the figure, produces the first of these two pulses, which is therefore referred to as Pulse 701. Pulse 702 is emitted at a later time than pulse 701, by system source 705, depicted on the left-hand side of the figure. The widths of Pulse 701 and Pulse 702 are shown as identical, and approximately matching the diameter of the target volume and the width of the collateral material through which it may pass, on either side of the target. In practice, these widths will not and need not perfectly match to carry out aspects of the present invention, and widths of the pulses need not exactly match the width of the target or collateral material through which they penetrate. For example, if the width of the collateral material is prioritized and/or keyed by the system, Protection area path-width directed pulses may be used such that the opposing beams overlap more completely at an instant of time in the collateral material area 713, while ensuring that no Protection or substantially no Protection occurs in the target area. Following the overlap/superposition period of time, in any approach, some ionizing radiation, albeit a lesser amount, will occur in the collateral Protection area 713, while the two pulses are not in the instant of perfectly matched overlap. Similarly, and preferably, a target-width influenced and/or keyed length and timed pulse may be used by at least one of the sources, or from both sources. Again, the pulses would be timed to intersect before or after the target, and, preferably, the instances of overlap for different pulse pairs would be at different, distributed points in the collateral Protection area, to more evenly distribute their Protection through that mass. Preferably, a distributable common denominator or factor of the target/radiation intersection path and its associated collateral matter intersection path is used and, more preferably, a small enough denominator or factor to allow even distribution of Protective superposition over a greater volume of collateral material. Protection can happen on both sides of the target mass or volume 707. After the first pulse pair, it is preferred that a new pulse follows, in the same relative timing as between the first pulse pair, and such that protective superposition again occurs on the opposite side of the target, and so on for additional pulses, from alternating sides, in similar timing, but preferably adjusted to distribute protection evenly across the collateral protection areas.

It should be noted that point-in-time-associated time/location indicators 715, 717, 719, 721 and 723—with notations $T_1$, $T_2$, $T_3$, $T_4$, and $T_5$—are relatively evenly spaced apart in time, but are preferably in increments necessary to achieve the relative locations indicated and discussed, given that the distances involved with a particular target mass and collateral area needing Protection. Preferably, a refraction model is also used by the system, allowing for correct timing and angles, which model may be tuned by the system according to live feedback (e.g., infra-red sensory data for indicating whether heating associated with ionizing energy is present) indicating whether Protective superposition is failing or not optimal.

Figure 8:
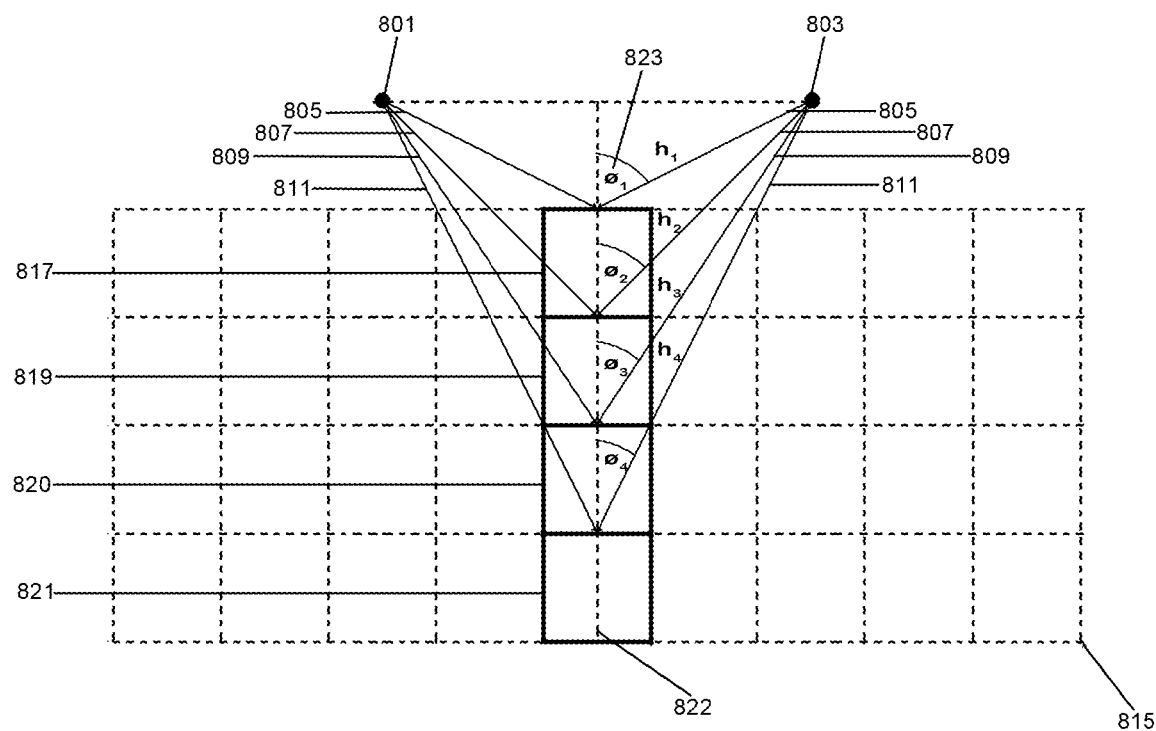
FIG. 8 depicts an informational storage system and media implementing aspects of the present invention.

FIG. 8 is a side-view of aspects comprised in an informational storage system and media implementing aspects of the present invention. Directable radiation sources 801 and 803 may direct beams of radiation along any of paired vector paths 805, 807, 809 or 811 (source 801 being capable of directing beams along the half of the paired vectors projecting from the upper left-hand side toward the lower right-hand side, and source 803 capable of directing beams along the half of the paired vectors projecting from the upper-right hand side toward the lower-left hand side of the figure). A multi-component readable and/or writable media 815 lies within the paired vector paths 805-811. Preferably, the paired vector paths 805-811 converge at or about the leading volume or features of media components, 817-821, currently being written or read by the system. Media components neighboring 817-821, which are not currently being written or read, are depicted with dashed lines, signifying their inactive state, because they are not the main focus of the figure. As discussed previously in this application, aspects of the present invention allow the converging pairs of radiation beams to vector sum and/or superpose with one another, with a net vector and/or changed frequency or other resulting characteristic centered along a resulting vector line 822, and in a direction toward the bottom of the figure. However, the source vectors which are, by themselves, weaker than their resulting vector, alone will pass through certain of the neighboring media components. As a result, a resulting vector may be sufficient to impart a greater effect, such as imparting a charge or charge differential, as in a changed magnetic condition or state, or causing a chemical reaction or photon amplitude-dependent effects in the media component through which it first passes, while being insufficient to impart the same effect on neighboring components. Such effects may be relatively transient, permanent, and/or readable by the system, depending on the media components selected. Wide enough source angles, such as those shown for components 817 and 819, along with a reflective or semi-reflective surface just above the convergence points of the summing vectors, may permit components within the path of the resulting vector, which are further downstream than the component targeted by a vector pair, to avoid reaching a critical affected energy as well. However, it is also possible, and with certain advantages such as cost of manufacturing, to optimize the array of media component sizes and reactivity (e.g., chargeable cells) and/or beam targeting angles and strengths, such that the naturally increasing vector sum percentage, balanced by the natural spreading and scattering of radiation the beam used, causes the read or write reaction to occur in the cell in which the beams converge, but not in any neighboring cell. Even more preferably, however, the reaction and charge differential leading to a read or write event within a media component is based at least partially on a local differential with neighboring media components. In other words, only when the resulting vector beam energy is both above a threshold and significantly greater than its neighbors, will the read or write event occur in that media component. This arrangement can be achieved, among other ways, by a writing event triggered by a charge diffusion (efflux) gate.

To illustrate the nature of the naturally increasing vector percentage in the instance of in-phase amplitude superposition, mentioned immediately above, as pictured, vectors 805 converge with an angle, shown as $\emptyset_1$ (823), of 63.43 degrees, which results in a vector sum (of its resulting superposed beam) that is 89.46 percent of either of the two even source vectors at the point of convergence. Assuming that the neighboring media components are tuned to the same combined wave critical reaction energy (or activation energy) for a read/write event, just below (but significantly below) the energy level of each source vector alone, the individual source vectors generally would need to lose slightly more than 10.54 percent of their passage across the upper corners of media component 817, to avoid an inadvertent read or write event in the neighboring components, assuming that no additional reflecting, refracting or absorbing features are also included along such stray vector paths from neighboring component activation, which additional features may be desirable to omit for cost reasons. An appropriate media and beam type, causing sufficient radiation scattering and absorption, could be chosen for that purpose. Alternatively, or in addition, a central reacting element, such as an antenna located in the center of a cellular media component, could be missed by the majority or a critical amount of such pass-through source vectors in the neighboring media components. Also alternatively, the media component cells could be other than square-shaped, or otherwise have facets that aid in reflecting or scattering vectors that do not proceed in the direction of the resulting combination centered on the line of the targeted media component's column, 822. In any event, however, the resulting vector itself must decrease in force as it proceeds to the next media component below the target media component, or the next media component (or, row thereof) below the target media component must be tuned to a higher reaction energy, to avoid an inadvertent read/write event. In this latter instance, the greater percentage sum of resulting vectors as convergence events proceed downward, for deeper read or write events, naturally aids in utilizing such higher reaction energies. But if the system utilizes the natural attrition of a radiation beam from scattering alone, a critical distance may be required from the sources to the first useable media row, such that the decrease in beam strength due to scattering and absorption may be balanced by the increasing resulting vector strength percentage allows a reaction that is within a range of source vectors that do not inadvertently cause a read or write event in cells other than the targeted cell. For example, if square media component cells are used, the distances shown for media component cells 819, 820 and 821 may be sufficient relative to the source separation, because the resulting summed vectors of the same strength beam would be 141.4 percent of the source beams at convergence for the beams converging at $\emptyset_2$, 166.4 percent for the beams converging at $\emptyset_3$ (or, 17.58 percent more vector sum percentage) and 178.9 percent for the beams converging at $\emptyset_4$ (or, 7.512 percent more vector sum percentage over the sum at $\emptyset_3$), Meanwhile, the source beam lengths (their distances traveled) increase 27.4 percent and 24.1 percent over the same two intervals, as determined by Pythagorean theorem. While these latter intervals, in source beam length, are greater, generally, the semi-exponential attrition due to beam scattering and absorption may be used to exaggerate or decrease the effect of those intervals. Using a beam and media type with a reverse square attrition due to distance, for example, the first interval results in a 38.4 percent decrease and the second interval results in a 35 percent decrease in beam strength due to scattering/absorption. To compensate for this difference, deeper tiers of levels of the media can be made more sensitive in their reaction energy or activation energy, such that they are activated despite the greater attrition to vector sum resultant vector ratio at those tiers. Alternatively, a medium and source beam with a more favorable attrition-with-distance profile may be chosen, than the example just discussed, which depletes with the inverse square of the distance from the source. As another approach, localized and/or periodic optical or other amplification may be used at points along the beam paths, to bring the attrition and vector summing into balance for activating individual cells. As another option, media component or cell length may increase as tiers/rows deepen (away from the source), with or without cell size fanning out and becoming wider horizontally, which is another alternative configuration, to allow a greater build-up of net affecting charge, or other reaction, in deeper cells. This aspect is demonstrated, among others, in more detail, in FIG. 9, below.

Depending on the nature of the media selected and the characteristics of its comprised elements, such as their refractive index and radiation scattering and absorption characteristics, optimized media components sizes and shapes may be selected that allow the activation of the media component or components targeted by converging wave beams, without inadvertently activating neighboring media components.

It should be noted that either the media or the sources may rotate around a central axis, or, to avoid moving parts, both may remain stationary while the strengths of sources vary to create the requisite vector sum at any media component targeted by vector convergence. Multiple sources, other than two, may also be used to increase selectivity of the appropriate media component(s) for a read-write event. In any event, it is preferred that the cells take on a concentered configuration, and that they be shaped for such concentricity, as further illustrated in FIG. 9.

Figure 9:
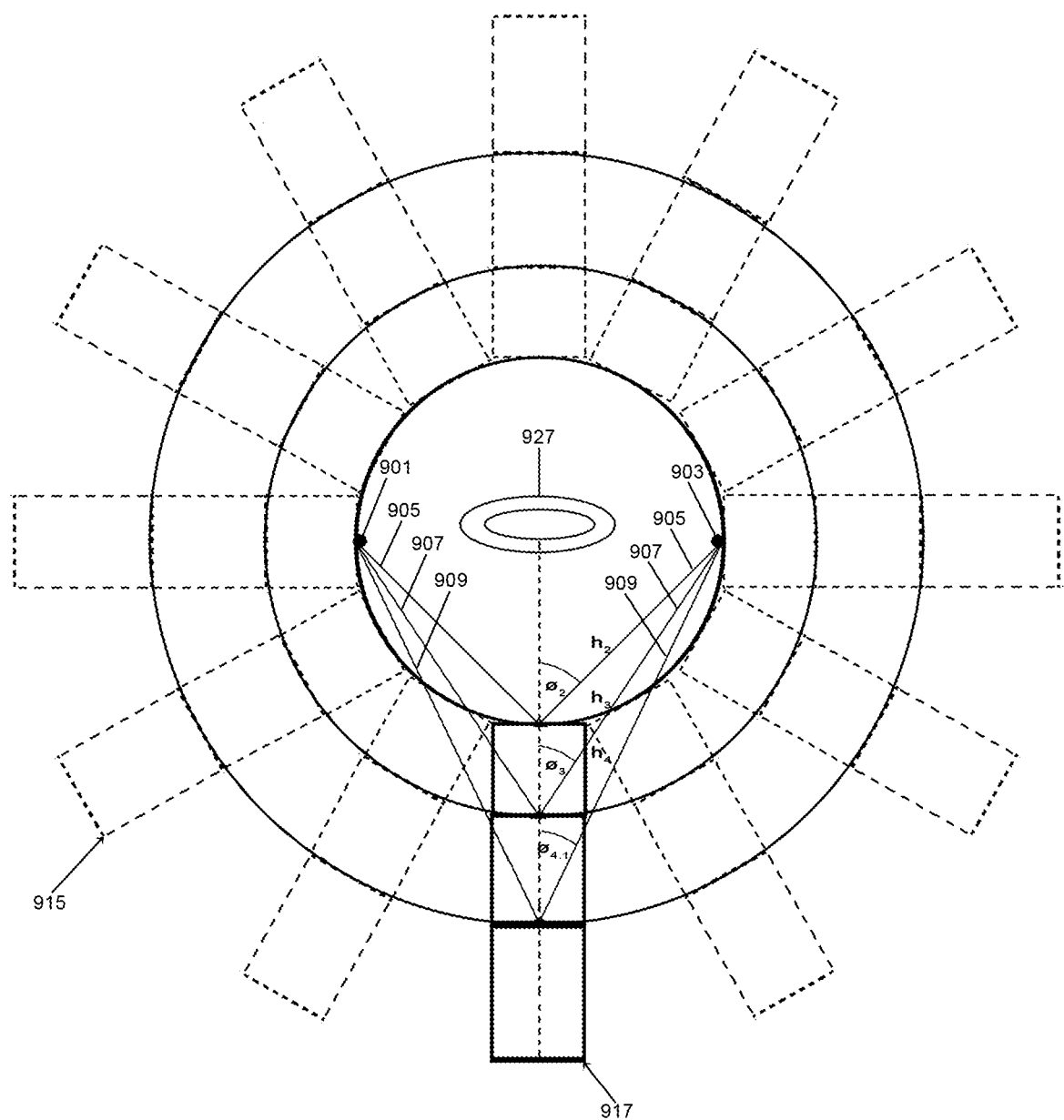
FIG. 9 depicts a more particular and preferred spatial configuration of an informational storage system and media implementing aspects of the present invention.

FIG. 9 depicts comprised parts of a storage medium and system according to aspects of the present invention. As with the system discussed with respect to FIG. 8, the system discussed with respect to FIG. 9 includes directable or directed electromagnetic radiation sources (in this instance, 901 and 903), and which may direct beams of radiation along any of paired vector paths 905, 907, or 909, among other pairings (not pictured) for read or write activities at deeper levels, away from the center between the sources (some of which levels are also, not pictured). As with the analogous sources in FIG. 8, source 901 is capable of directing beams along the half of the paired vectors projecting from the upper left-hand side toward the lower right-hand side, and source 903 is capable of directing beams along the half of the paired vectors projecting from the upper-right hand side toward the lower-left hand side of the figure. However, FIG. 9 further illustrates several additional aspects of the present invention, only some of which were discussed above, with respect to FIG. 8. First, sources 901 and 903 may be swiveled, as a pair, along a circular path for their mounting, with respect to its circular grid array of media components 915, which also point radially outward from the center between the sources. A computer system (not pictured) may direct an actuator (also not pictured) to swivel either the sources on their mounting or the grid array on their mounting, in appropriate stopping points to allow the sources to evenly address the center of the leading volume of a row of grid components, which may then be considered active, such as shown active row of media components 917. A sensor, 927, may be used for both reading and writing confirmation readings, which indicate the read/written condition of a media component. Specifically, when a component has been written by the system, a charge density or other reaction condition may be detectable by return radiation which reflects directly back from each surface between individual media components (shown as three per row, in this instance), and therefore passes back through the media in that cell. This configuration permits the sources to remain in a semi-fixed orientation with respect to one another, while permitting the reading of a wide variety of media cells. A greater density of smaller media component cells than that pictured may be used, including smaller cell rows in greater numbers and at more angles, and/or with additional sets into the page, i.e., along a z-axis of the figure (preferably, serial with the previous set, by a single strand, spiral configuration, may be used, to allow infinitely expandable storage, particularly with spiral add-on units that may be fastened together, to lengthen the spiral). In this instance, an actuating mechanism for both spinning and drawing the media with respect to the sensor and source array should be used. A spherical array may also be used by simply extending the array, as it is shown in FIG. 9, in three dimensions, in which case the sensor source center piece may be spherical, rather than circular. Alternatively, sensors may be placed on the far side of a row of media components, among other possibilities, in addition to or instead of the location shown for sensor 927, and may be fixed in position relative to the mounting for the sources. In that instance, reflection back by media components is not required for read/write scanning/confirmation.

FIGS. 10-15 relate to a system implementing aspects of the present invention related to encryption and decryption of message or information-carrying waves, such as electromagnetic radiation. To implement these aspects, information-carrying modulation of waves is used. Preferably, and as demonstrated in the figures, amplitude modulation of two carrier source waves is used, but it should be understood that any form of wave modulation to carry information may be used, including, but not limited to, frequency modulation, period modulation, polarization modulation, a type of modulation based on the instantaneous and potentially infinite warping of the direction of an electromagnetic sine wave at any point or the derivation or integration of all such points, and any number of source waves may be used.

Figure 10:
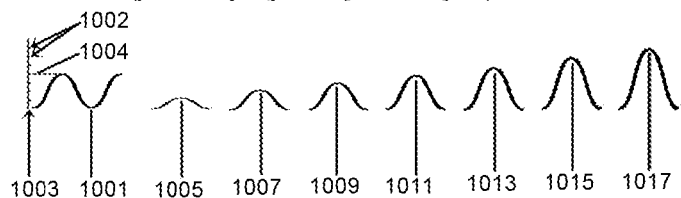
FIG. 10 is a graphical depiction of an example wave amplitude modulation alphabet, which may be used to create Encrypted Source Beams from a carrier beam and a modulation beam in an encryption/decryption system in accordance with aspects of the present invention.

FIG. 10 is a graphical depiction of an example wave amplitude modulation alphabet which may be implemented in a modulated carrier source wave that may be used in certain encryption/decryption aspects of the present invention. A carrier wave, preferably of a substantially constant amplitude, frequency, polarization (especially in comparison to any of the Encrypted Source Beam waves generated by the system, such that these characteristics are in common with each source wave encrypted and/or decrypted by the system) may be provided by the system. Part of a such a carrier wave is shown as 1001, and a ruler 1003 with dashed line 1004 which measures the crest (the amplitude, or substantial highest concentration of particles, or particle location probabilities, depending on the type of wave used) are depicted. The ruler 1003 also depicts various possible levels of amplitude modulation of the carrier wave, at tick points (for example, tick points 1002) corresponding with amplitude levels 1 through 7 (the level of the second tick point or level up from the bottom of the ruler being twice the amplitude level of the first, and the level of the third tick/level up from the bottom of the ruler being three times the amplitude level of tick/level 1, and so on.) The potential amplitudes of such a modulated wave are demonstrated by wave sections 1005, 1007, 1009, 1011, 1013, 1015 and 1017, each of which corresponds to one, and only one, of the ruler tick points. Including the level of the unmodulated carrier wave, the depicted modulation alphabet for one source wave therefore comprises 7 units (symbols or keys) which may be output in a modulated source wave. For convenience, we may refer to amplitude modulation levels 1005, 1007, 1009, 1011, 1013, 1015 and 1017 as energy or amplitude levels/symbols 1, 2, 3, 4, 5, 6 and 7, respectively, each matching a tick/level on the ruler. It should be understood that, although an amplitude modulation alphabet is pictured as an example, any form of wave modulation to communicate data may be used, alternatively or in addition to the amplitude modulation example pictured.

Figure 11:
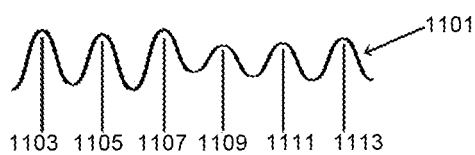
FIG. 11 is a graphical depiction of an example Encrypted Source Beam wave using the alphabet of FIG. 10, and generated from a carrier beam wave, such as that discussed in relation to FIG. 10.

FIG. 11 is a graphical depiction of an example modulated source signal 1101, generated by the carrier beam, and using the alphabet of FIG. 10. Modulated source signal 1101 is modulated at particular regions 1103, 1105, 1107, 1109, 1111 and 1113. In this instance, one may see, with reference to the modulation levels discussed with reference to FIG. 10, that, reading from right to left (from 1113 to 1103), that the modulated source signal comprises the following symbols, in the following order: amplitude level/symbols 5, 4, 3, 7, 6, 7.

Figure 12:
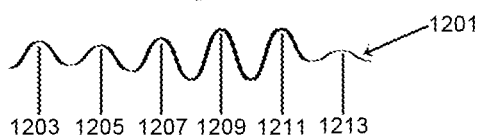
FIG. 12 is a graphical depiction of another example of an Encrypted Source Beam wave, generated by a substantially identical carrier beam as used in FIG. 11, and also using the symbolic alphabet of FIG. 10.

FIG. 12 is a graphical depiction of another example modulated source signal 1201, generated by a substantially identical carrier beam as used in FIG. 11, and also using the symbol alphabet of FIG. 10. Modulated source signal 1201 is modulated at particular regions 1203, 1205, 1207, 1209, 1211 and 1213. In this instance, one may see, with reference to the modulation levels discussed with reference to FIG. 10, that, reading from right to left (from 1213 to 1203), the modulated source signal comprises the following symbols, in the following order: amplitude level/symbols 1, 6, 6, 4, 2, 3.

Figure 13:
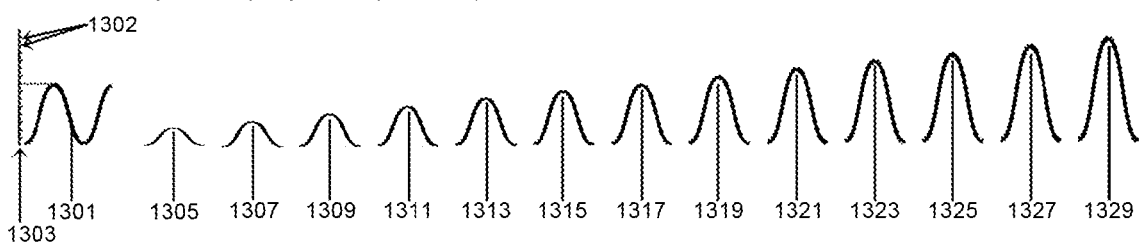
FIG. 13 is a graphical depiction of an example of a resulting wave amplitude modulation alphabet, resulting from combination of multiple (in this instance two) Encrypted Source Beam waves.

FIG. 13 is a graphical depiction of an example of a resulting wave amplitude modulation symbol alphabet, resulting from the combination of multiple (in this instance 2) Encrypted Source Beam waves. As will be explained in greater detail, with respect to FIG. 15, a system in accordance with aspects of the present invention may cause 2 modulated source waves, such as those discussed with respect to FIGS. 11 and 12, to converge at a particular point, region, angle, period and timing such that, as they converge at a particular point or region, they generate a superposed vector sum of a resultant wave that is in phase with the each of the two source waves, which are, themselves, in phase. In the instance of the symbol alphabet depicted in FIG. 13, the angle of convergence may be 45 degrees, with the source beams of equal strength, converging at the strengths depicted in FIGS. 11 and 12. As a result, the vector sum of the two constituent source waves would be approximately 71 percent, if each were unmodulated, or 35.5 percent of whatever modulated power level each source wave contains. Given that each source wave, in the instance of a two-source wave encryption/decryption language and system, has 7 symbol/power levels, a resulting alphabet for a resulting, decrypted and vector summed wave will have 13 possible symbols/power levels, including the level obtained by 2 unmodified carrier source waves. (Namely, the resultant amplitude alphabet will be from the minimum combination of two source wave level-1 symbols (which we may call level 2 of the resultant wave in terms of power level, but level 1 in terms of the resultant wave lexicon) and a maximum combination of two level-7 source wave symbols (which we may call level 14 in terms of power level, but level 13 in terms of the resultant wave lexicon.) The result of what the two unmodulated carrier source waves would be is shown as resultant carrier combination 1301. A ruler 1303 depicts 14 evenly-divided power levels at ticks (such as 1302), 13 of which, as discussed above, are possible resulting power levels and symbols, which are shown as wave sections 1305, 1307, 1309, 1311, 1313, 1315, 1317, 1319, 1321, 1323, 1325, 1327 and 1329, each of which corresponds to one, and only one, of the ruler tick points. As discussed above, wave section 1305 corresponds with the combination and superposition of two level-1 source wave sections. Wave section 1307 corresponds with the combination of one level-1 source wave section and one level-2 source wave section, and so on, exhausting each in-phase superposition possibility.

The symbols to be employed by a control system implementing aspects of the present invention may be selected for delivery at a target location in accordance with a varied, randomly-generated or semi-randomly-generated combination algorithm. In other words, instances of the same symbol in a resultant signal can be achieved by an unlimited variety of source symbol combinations selected by the control system, each of which is selected to sum to the desired resultant symbol at the target location. The control system may be programmed with an algorithm assigning various, preferably different and non-repeating source symbol combinations to make hacking impossible. Fractional or even source levels may be assigned to generate the source and resultant signals to yield a greater number of possible combinations. More than two sources may also be used, yielding even stronger encryption, with three or more source symbols superposing in a manner planned by the system at the target to yield the same resultant alphabet. The combination algorithm may be more complex, and difficult to hack, using more sources.

The location-based encryption methods discussed herein can be used in combination with other forms of encryption, for example, by use of a shared key or cipher to further encode the resultant signal. The same control system may be used to apply each layer of encryption.

Figure 14:
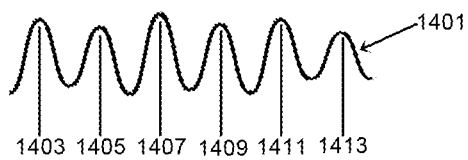
FIG. 14 is a graphical depiction of an example Decrypted Result Beam wave, that might be generated by the two example Encrypted Source Beam waves of FIGS. 11 and 12, and implementing the alphabet of FIG. 13.

FIG. 14 is a graphical depiction of an example resultant signal, that might be generated by the two example modulated carrier beams of FIGS. 11 and 12, and implementing the alphabet, of FIG. 13. As a result, combining Encrypted Source Beam waves 1101 and 1201, assuming all of the necessary identical conditions discussed above, results in resulting wave pattern 1401. From right to left, the now combined and decrypted word, phrase or other packet of symbols comprises the following symbols, in the following order: amplitude level/symbols (from the possible resultant alphabet of FIG. 13: amplitude level/symbols: 6, 10, 9, 11, 8, 10.

Through a separate encryption process (not pictured) such a resultant, unencrypted phrase may be broken down randomly by a computer hardware and software system into random factors or subtraction results, within the integers permitted by the source alphabet, and then may be used to modulate the source carrier waves in an encryption process that is difficult to break, except within the intended recipient area targeted by the Encrypted Source Beam wave vectors.

Figure 15:
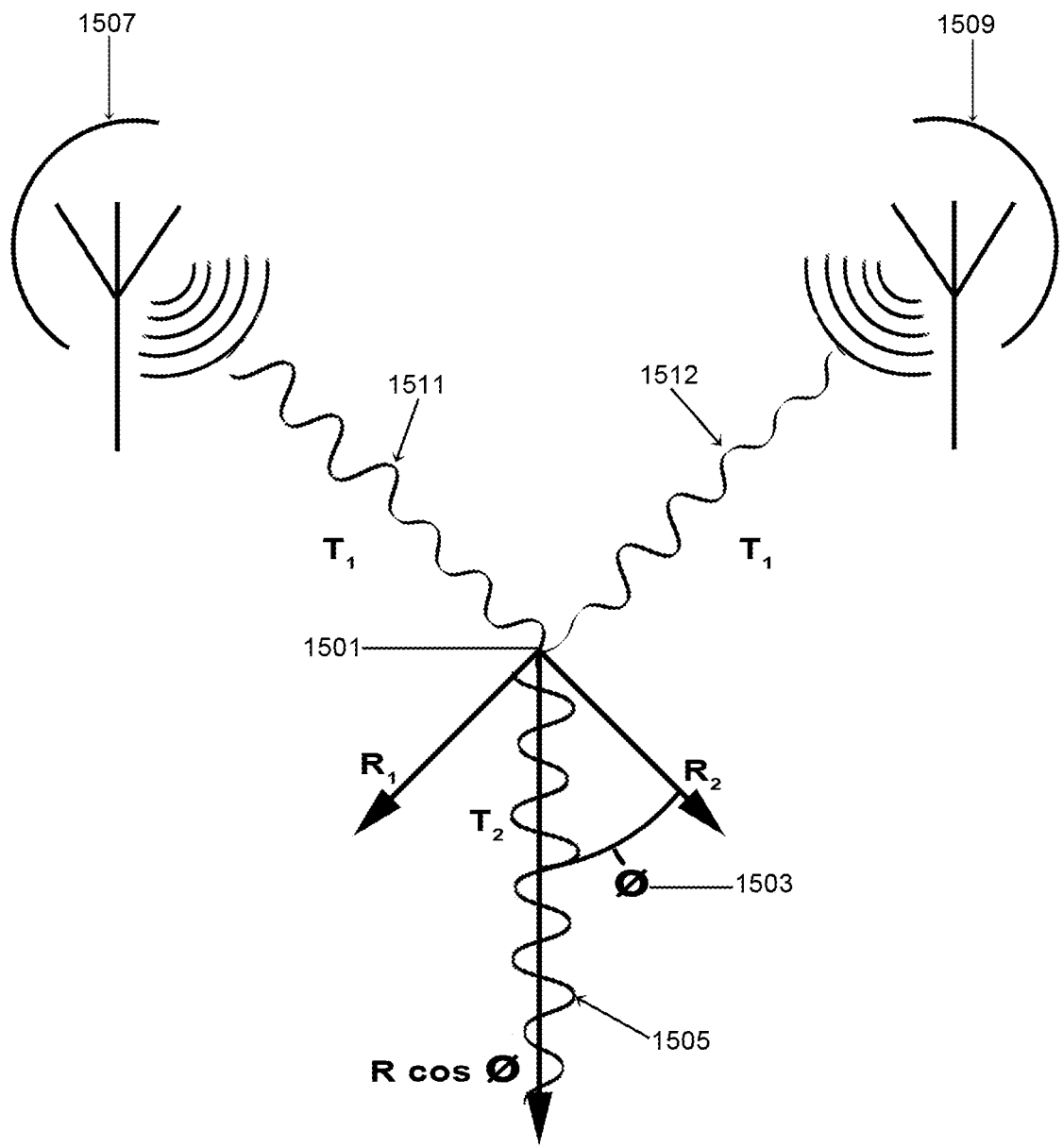
FIG. 15 is a graphical depiction of a part of an example radio frequency signal modulation, encryption, transmission, receiver and decryption hardware system and related techniques, in accordance with aspects of the present invention.

FIG. 15 is a graphical depiction of a part of an example radio frequency signal modulation, encryption, transmission, receiver and decryption system, in accordance with aspects of the present invention. In this example, directional wave transmission broadcast antennas 1507 and 1509 may broadcast waves of the same period, polarization and other important characteristics for carrying out superposition aspects of the present invention, as discussed elsewhere in this application. Source waves 1511 and 1512 may be substantially identical to the waves depicted and discussed with respect to FIGS. 11 and 12, and may be aimed as shown by the directional antenna sources 1507 and 1509, such that they substantially converge at a point 1501, at an angle ø, 1503, which, in this instance, is 45 degrees, as was the case in FIGS. 1-3. As a result, and as discussed with respect to FIGS. 13 and 14, their resulting vector sum is a Decrypted Result Beam wave substantially identical to that shown in FIG. 14, and shown in FIG. 15 as 1505. Using aspects of the present invention, if the location of a desired receiving area is known, a known array of transmission or other wave sources, such as 1507 and 1509, can be oriented by a computer system to transmit randomized source alphabet components to that desired receiving area, such that they create the decrypted vector sum signal in that area only. Although a simple, even spatial division is shown in FIG. 15, it is also possible to adjust the encrypted transmission for any distance by initiating the wave from the more distant location earlier, by the correct amount of time such that its transmission across the distance to the receiving area is simultaneous with the transmission from another, closer source. Power levels may also be appropriately adjusted, such that the desired or necessary combination levels are achieved. Any number of alternative source and resultant alphabets may also be used, and source alphabets may be unevenly applied to result in the correct resultant wave language at given distances and transmission and receiving locations.

Rather than rely on the correct alignment of two Encrypted Source Beam waves perfectly converging at the intended receiving and decryption superposition target, a variety of spaced, identical different Encrypted Source Beam waves may be aimed at the receiving area, which may be at a variety of angles to cover the location and orientation of the intended receiving/decryption hardware. Using this technique, regardless of the perfection of in-phase superposition in any one instance of wave convergence, at least one such set of superposing vectors will correctly sum to a valid combination, as may be quickly determined and selected for translation into a message by a receiving device, based on whether isolated symbols of the correct proportions are being received, matching a valid decryption vector sum library, such as that described with respect to FIG. 12.

The system may, alternatively, receive just one Encrypted Source Beam wave which, when combined properly with a known second Encrypted Source Beam wave form, which may be regenerated locally, by the receiving hardware, yields a Decrypted Result Beam.

Figure 16:
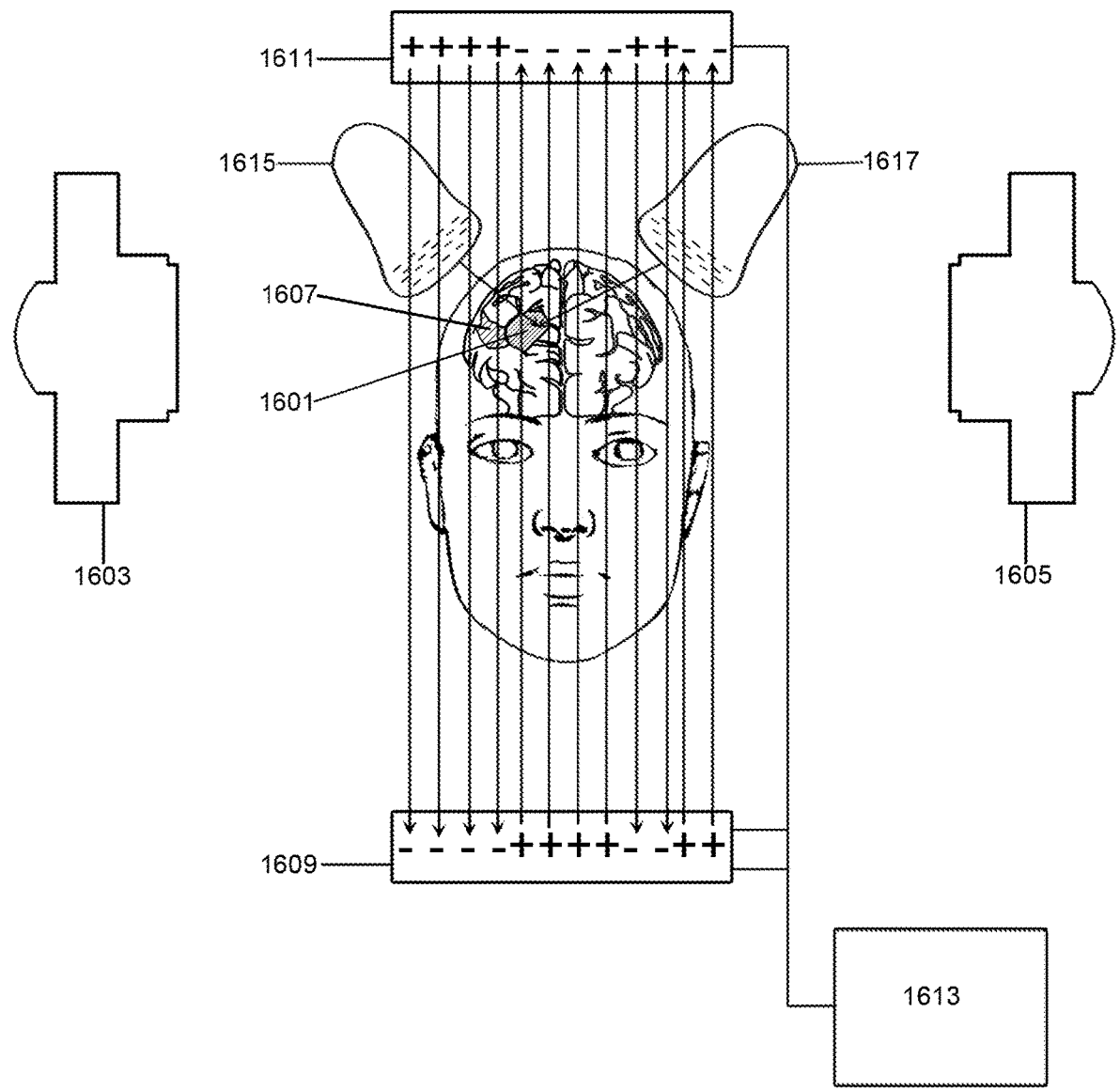
FIG. 16 depicts the head and brain of a human patient and another exemplary hardware system carrying out aspects of the present invention related to radiation delivery.
Figure 17:
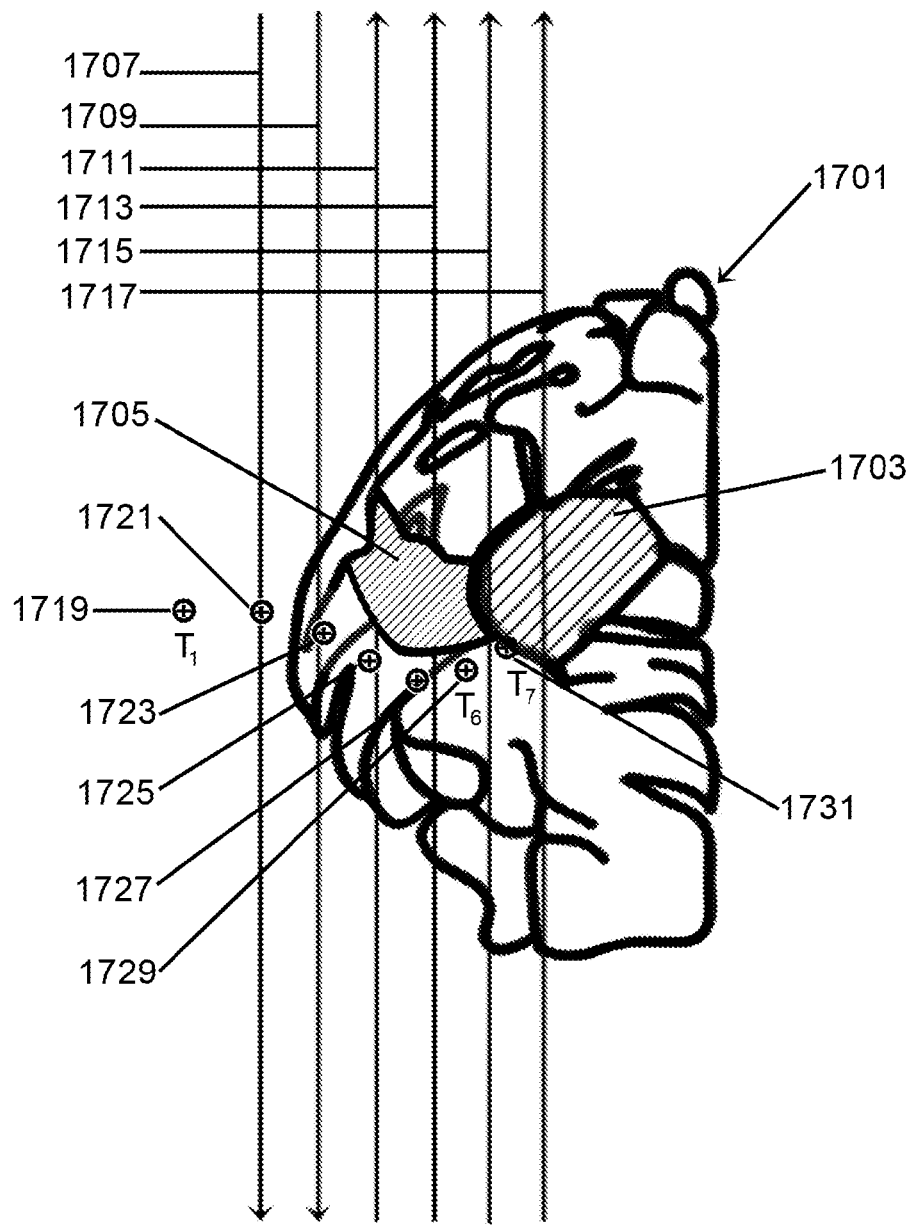
FIG. 17 depicts a detailed outline of a structural target within the brain of human patient, and further depicts a sequence of exemplary radiation conditions that may be controlled and monitored by a hardware system according to aspects of the present invention.

FIG. 16 depicts the head and brain of a human medical patient, and another exemplary hardware system carrying out aspects of the present invention related to radiation delivery. Although the context of patient Treatment is given for FIGS. 16 through 18 and certain other figures, it should be understood that any target for ionizing or other critical energy level targets or subjects, with collateral structures and media, may be Treated in similar ways according to most aspects of the present invention. In FIG. 16, target volume 1601 is to be subjected to ionizing radiation. Examples of such targets include, but are not limited to, malignant or benign tumors and neurological source structures for undesired tremors or seizures. Directable radiation sources 1603 and 1605 each face the patient's cranium, within which the target volume is embedded, and each radiation source may focus a radiation beam on parts of the target 1601, irradiating it simultaneously. Also pictured is a relatively important, healthy area of the subject's brain, 1607, nearby the target tumor. A physician and/or analytical system may have determined that 1607 is especially important to the patient's health and function, in comparison with other nearby regions of the brain. As will be explained in greater detail with respect to FIG. 17, due to 1607, and other relatively important structures, there may be no easy, straight-line path from a source, such as 1603, to a target area, such as 1601. However, magnetic or electrostatic field generators 1609 and 1611 may be used to create magnetic and/or electrostatic fields of multiple different side-by-side orientations, which may even be directly opposed from one region to another. Preferably, magnetic and/or electrostatic field generators 1609 and 1611 work in conjunction with one another, as shown, reinforcing the desired characteristics of desired magnetic and/or electrostatic fields in the patient. A control system 1613, such as the system discussed in greater detail with respect to FIG. 19, may command magnetic and/or electrostatic field generators 1609 and 1611, and their individually actuable regions, to generate the characteristics of the desired magnetic and/or electrostatic fields. In addition, local charging units 1615 and 1617 may be used, and controlled by control system 1615, to impart a local charge differential on nearby or targeted areas, as by passing off electrons into the tissues or drawing electrons from tissues towards them, for example, by conduction or creating a dipole, with the same net charge, in the tissue, but with localized regions of increased positive or negative charge. Although FIG. 17 depicts two instances each of radiation sources, magnetic and/or electrostatic field generators and charging units, it should be understood that a wide range of device arrays may be used to carry out aspects of the present invention. For example, anywhere from 1 to infinity charging units, of any conformational shape, may be used. In addition, if particle therapy is used, a single radiation source may be used or, an infinite number of sources in a complementary spatial array, such as a concentric focal array, may be used with any form of ionizing radiation for carrying out many aspects of the present invention. Similarly, a single, wrap-around magnetic or electrostatic field generator device(s) or unit(s) may be used, or many multiple instances of such generators, dedicated to generating different magnetic field lines in different regions of the subject which may be curved or otherwise shaped differently than the straight-path fields depicted in FIG. 16, while still directing radiation toward intended targets and around structures that need protection from radiation energy transfer.

Turning to FIG. 17, the significance of the electrostatic and magnetic fields and charge differentials generated by aspects of the invention discussed with reference to FIG. 16 can be better understood in the context of further aspects of the invention. FIG. 17 depicts a partial view of the same human patient subject discussed with respect to FIG. 16, including a detailed outline of a structural target within the brain of the human patient. In addition, FIG. 17 depicts a sequence of exemplary particle radiation conditions that may be controlled and monitored in accordance with aspects of the present invention. The right hemisphere 1701 of the patient's brain is included in FIG. 17, and shown in greater detail than in FIG. 16. The target region volume is shown in greater detail as well, as 1703. A critical healthy structure of brain material, to be Protected from ionizing radiation, is shown as 1705. A particle emitted by a beam of particle radiation, with a particular charge, such as a proton, is shown at different positions over time as 1719 through 1731, and passes through magnetic and/or electrostatic field lines 1707-1717. 1719 through 1731 illustrate the charged particle's location at even time intervals, and therefore, map its trajectory through the patient's brain, which trajectory is, generally, from the left-hand side of the figure toward the right-hand side of the figure. 1719 depicts the location of the positively-charged particle, such as a proton, at the first point in time considered by the figure, which point in time may be called $T_1$. Progressing to the second point in time, the same particle's position is illustrated an instant later (i.e., the amount of time it takes the particle to travel the distance depicted, which is about 1 centimeter at its current speed, at about 30 to 40% of the speed of light), at a point in time that we may call $T_2$ (shown as particle location 1721). As can be seen by the relatively constant vertical position of the particle between positions 1719 and 1721, the particle's initial velocity, at $T_1$ is almost entirely in a horizontal direction, toward the right-hand side of the figure. However, at particle location 1721, the particle proceeds into an electric and/or magnetic field, depicted by electrostatic and/or magnetic field line 1707, which flows generally from the top to the bottom of the figure. By convention, the electrostatic and magnetic fields are depicted by arrows showing the direction of force that would be applied to a positively charged particle at the location of the arrows. Thus, because electrostatic and/or magnetic field line 1707 flows from the top of the figure, toward the bottom of the figure, the positively charged particle begins to accelerate in that direction, and its path begins to curve around the critical brain component 1705, as dictated by the system, optionally, with magnetic field tuning based on live feedback concerning the particle, the stream of related particles' path from the same source. As the particle continues to proceed generally from the left to the right-hand side of the figure, and arrives at position 1723, it again is immersed in an electrostatic and/or electromagnetic field line that forces it downward, its acceleration in that direction continues, and its partial velocity in that direction builds further. As the particle continues to progress at a relatively constant horizontal velocity, and maneuvers around critical feature 1705, it enters a reversed electrostatic or magnetic field at point 1725, as shown by line 1711, which flows from the bottom to the top of the page. At this point, the particle's downward velocity has accumulated appreciably, and the reversed field indicated by magnetic line or electrostatic field line 1711 begins to decrease, but does not yet immediately arrest, that vertical downward velocity component. As a result, the particle continues to curve around critical feature 1705, as planned by physical models incorporated in the system's Treatment plan, based on the mass and electromagnetic properties of both the fields and the particles. As the particle approaches location 1727, it remains in an electrostatic and/or electromagnetic field flowing vertically from the bottom to the top of the page. At this point, the particle has successfully circumnavigated the widest point downward, vertically, of critical feature 1705 and the particle reaches the apex of its curve as its downward vertical velocity is reduced toward zero by the electrostatic and/or magnetic field. Next, the particle proceeds to gain a partially upward velocity by continued acceleration of the electrostatic and/or magnetic field, which continues to flow in that direction, at position point 1729. At this point, the particle may be thought of as starting to steer toward the target location 1703, while continuing to curve around critical feature 1705, which is Protected from the otherwise straight-line path of the particle. To further assist in attraction to the correct target location, a charging device (not pictured) such as charger 1617 from FIG. 16, may impart a negative charge on structures near, and to the upper-right hand side of target 1703, by, for example, conducting electrons into tissue in that region. By positional point 1731, the particle flows into the target volume, while continuing to accelerate upward. While this may be desired to ensure that the greatest possible amount of target material lies in the particle's path, increasing the likelihood that it will ionize material there, for example, at the end of a Bragg curve, it may also or otherwise be desirable to alter the electrostatic and/or electromagnetic field upon entering the target, such that the path becomes further curved and, preferably, spiral—which spiral path turns inward or otherwise is confined against exiting the target material until ionization has occurred in target volume 1703.

Figure 18:
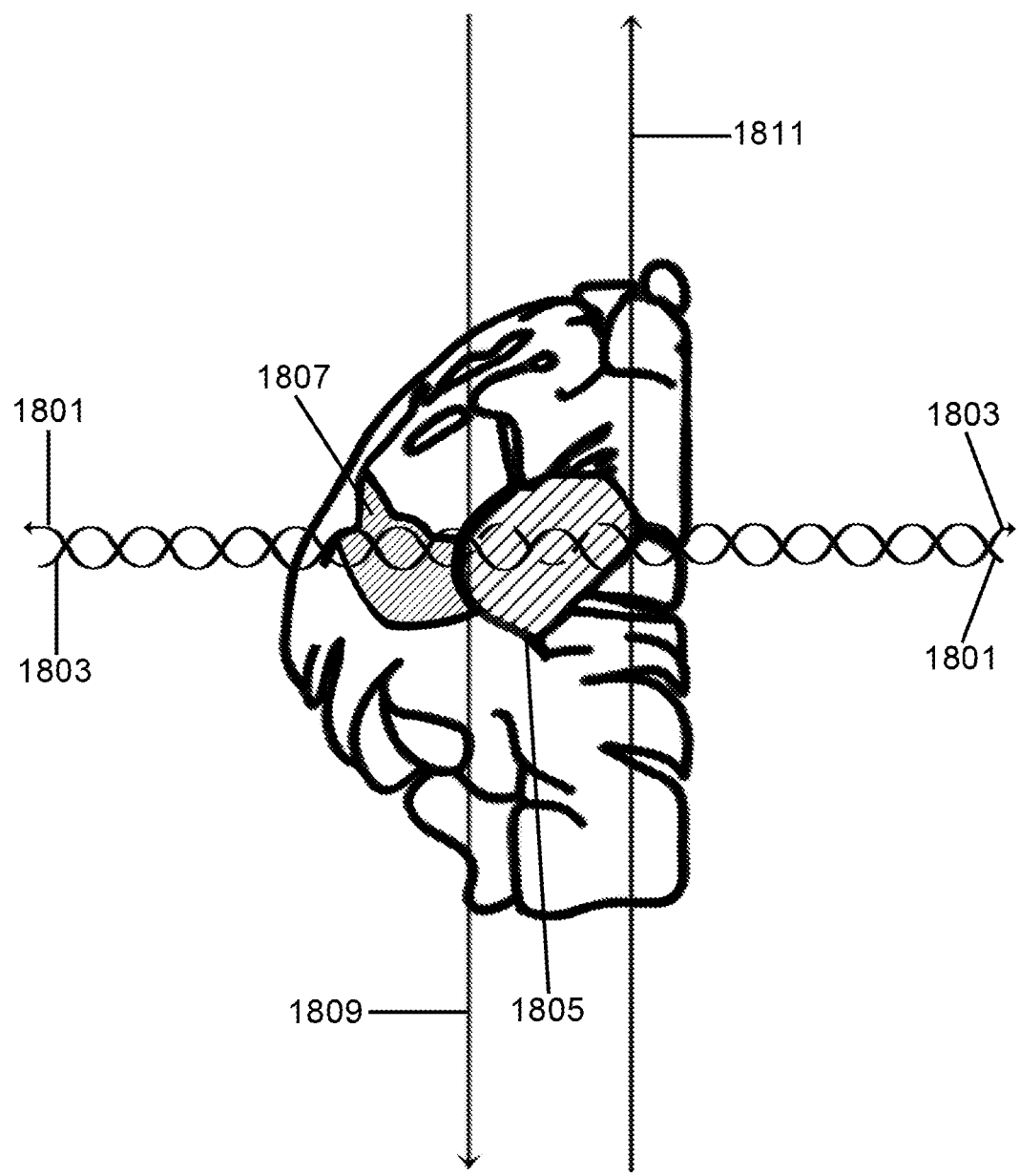
FIG. 18 also depicts a detailed outline of a structural target within the brain of human patient, and depicts another sequence of exemplary radiation conditions that may be controlled and monitored according to aspects of the present invention.

FIG. 18 also depicts a detailed outline of a structural target within the brain of a human patient, and depicts another sequence of exemplary radiation conditions that may be controlled or monitored according to aspects of the present invention. More specifically, FIG. 18 depicts two beam waves of ionizing electromagnetic radiation, 1801 and 1803, emanating from opposing directions, with the same period, preferably in counter-phase (180 degrees out-of-phase), and emanating from their sources with the same relative polarization and amplitude. Electrostatic and/or electromagnetic fields are again created by magnetic and/or electrostatic field generators, such as 1609 and 1611 depicted in FIG. 16, and create two discrete, exactly opposed electromagnetic fields: 1) an electromagnetic field applied upon the left edge where beam 1803 enters the target volume 1805 and/or exits critical structure 1807, and 2) an electromagnetic field applied upon the right edge where beam 1801 enters the target volume 1805 and or exits its collateral brain structures to the right. The former of these fields is described by electrostatic or electromagnetic field line 1809, and the latter of these fields is depicted by electrostatic or electromagnetic field line 1811. In this way, because electromagnetic waves shift their polarization when passing through a medium when subject to an externally-applied magnetic field (a magneto-optic effect), opposing, matched waves may better counter one another on either side of the target volume, creating a more effective standing wave that does not transfer ionizing radiation, but each wave entering the field at one edge of the target volume is brought out of phase with the opposing wave while passing through the target region, and may be brought back into the same polarization to again Protect collateral material upon exit at the other end of the target volume by the opposite magnetic and/or electrostatic field on the other side of the target volume. Simultaneously, the same fields may bring the two waves back into phase upon exit, by reversing the process that brought each of them out of phase upon entrance. Additional sensors (not pictured) may test, or periodically test, interference levels in the collateral tissues, by testing methods discussed elsewhere in this application, and adjust characteristics of the fields or sources (or add or adjust instances of them) to optimize Protective interference in the collateral material, especially, critical regions, and ionizing radiation in the target.

Magneto-optic effects may also be used in conjunction with other aspects of the present invention, such as those aspects discussed in relation to FIG. 5, to slow the propagation of the Treatment Beam of one source, with beam waves of one chirality, as it passes through the medium and magnetic field, in comparison to a Treatment Beam from another source, with waves of the opposite chirality. In this way, the two waves may be initially out-of-phase, when passing through collateral or critical structures, and then brought in phase when passing into a target structure.

In any radiation source configuration covered in this application where, as in the aspects covered in FIG. 18, two sources face one another and deliver pulses of energy substantially toward one another, other aspects may be used to protect each source from radiation emanating from the source opposing it—such as a variable shielding. Preferably, an absorptive shutter, which is absorptive on the side facing the radiation from the opposing source, closes at the correct time and for the correct duration to absorb any pulse received from the opposing source, and then re-opens to allow the source with the actuated shutter to emit its own pulse. The timing may be orchestrated and adjusted based on feedback from sensors indicating whether opposing radiation is properly blocked. Alternatively, or in addition to such shielding, the sources themselves may avoid such opposing radiation by movement—for example, a juke to dodge the arrival of an opposing pulse, or, due to rotation of the sources, wherein superposition paths at the target shift from convergence point to convergence point around the volume, the pulses may be timed by the system to miss any other source, and, instead, hit neighboring electromagnetic shielding.

FIG. 19 is a schematic block diagram of some elements of a control system 1900, preferably incorporating a machine-readable medium, that may be used to implement various aspects of the present invention, other elements of which are depicted in FIGS. 1-18 and 20-23. The generic and other components and aspects described herein are not exhaustive of the many different systems and variations, including a number of possible hardware aspects and machine-readable media that might be used, in accordance with the invention. Rather, the system 1900 is described here to make clear how aspects may be implemented.

Among other components, the system 1900 includes an input/output device 1901, a memory device 1903, storage media and/or hard disk recorder and/or cloud storage port or connection device 1905, and a processor or processors 1907. The processor(s) 1907 is (are) capable of receiving, interpreting, processing and manipulating signals and executing instructions for further processing and for output, pre-output and/or storage in and outside of the system. The processor(s) 1907 may be general or multipurpose, single- or multi-threaded, and may have a single core or several processor cores, including microprocessors. Among other things, the processor is capable of processing signals and instructions for the input/output device 1901, analog receiver/storage/converter device 1919, and/or analog in/out device 1921, to cause a user interface to be provided or modified for use by a user on hardware, such as, but not limited to, physical hand controls (e.g., 3-D hand sensor, scalpel emulator, endoscopic instrument or joystick control) and/or a personal computer monitor or terminal monitor with a mouse and keyboard and presentation and input software (as in a GUI).

For example, "window" presentation user interface aspects may present a user with the option to target particular locations of visual emulations of a target model, which lead radiation sources to correspondingly target emulated and modeled real targets, based on live feedback, such as imaging and the detected movement of painted or edge/boundary detected targets within a collateral medium or material. As another example, the user interface and hardware may allow a user to manipulate a "virtual scalpel" in real time, and with reference to a live model depicted on a computer monitor and presenting instantaneous information from an Nuclear Magnetic Resonance Imaging ("MRI") or X-ray radiographic (e.g., CAT scan) machine, which may allow a surgeon to apply ionizing energy to (or "lance") particular areas of a target, in particular shapes and sizes or pulses and pulse rates to substantially ionize matter, which size and shape may be given a hardness of edge, tolerance, and strength, all individually controllable by a user or surgeon. A virtual scalpel or other ionizing/Protecting tool may include a shaped cursor which may be semi-transparent, and may allow the user/surgeon to plan and view a portrayed path for the planned future ionization or other, for example actual, robotic, surgical lancing or surgical subject manipulation, before it is actually implemented on a subject (which execution can be done in parts or degrees or completely, with a separate, later command to the system). This surgical or manipulation path planning may be done with a cursor or other display, such as a computer monitor, or depiction/control hardware and techniques (e.g., 3-D physical contour and cutting or manipulation emulation device). In any event, a surgeon may create a path of planned movement for manipulation or lancing by programming such a path and/or by first executing the path in virtual or real space and, optionally, reviewing a depicted path based on that execution, and, if satisfied with the characteristics of the movement(s) of the executed path (e.g., direction(s), length(s), breadth(s), pressure(s), actual or real tissue reaction(s), location(s), size(s) of lancing or projected lancing, or blunt instrument trial of where lancing will take place), all of which characteristics may be displayed numerically or graphically as an attribute of a depicted path in a display as a "Planned Path," representation, the surgeon may then choose to have the path executed on the patient/target tissues. Optionally, before choosing to execute the path, the surgeon or other user may choose to save a file composed and capable of executing the characteristics of the movement on the system. Also optionally, the surgeon or other user may elect to modify individual, several or all characteristics of the path over any part of the path's progression, again may choose to save such a file, and again may choose to execute the path, which may be executed at different speeds along the path or even with a graduated acceleration device, which may be stopped at any time during observation of the movement. The system may automatically, or at the surgeon's direction, adjust the path or path segments for unintended hand tremor by smoothing or drawing more graduated curves and movement accelerations along progressions or as to characteristics of the path. The system may automatically, or a user may direct it, to generate Protective radiation in greater, lesser or other amounts that better interfere and Protect against ionizing radiation, for Protected collateral areas, as well, as another example, based on live feedback concerning the amount of Protection actually occurring through interference, as sensed by the system, and/or based on physical models, including refraction models. The processor 1907 is capable of processing instructions stored in memory devices 1905 and/or 1903 (or ROM or RAM), and may communicate via system buses 1975. Input/output device 1901 is capable of input/output operations for the system, and may include and communicate through innumerable input and/or output hardware, and innumerable instances thereof, such as a computer mouse, MRI machine, X-Ray radiography device, robotic surgical actuator(s), magnetic field creators or modifiers/oscillators (and magnetically-actuated, locatable nano-particles or manipulation devices that are systemically or locally available in patients, e.g., particles with abrasive surfaces that may spin, expand, grab, cauterize through electric charge, in an oscillating magnetic field and that may also react to markers on targets, available through injection into the patient), such as communications antenna, electromagnetic radiation source(s), keyboard, networked or connected second computer, camera or scanner, a multi-tiered information storage device, such as that described with reference to FIGS. 8 and 9 (including its actuators and read/write apparati), mixing board, real-to-real tape recorder, external hard disk recorder, additional movie and/or sound editing system or gear, speakers, external filter, amp, preamp, equalizer, computer display screen or touch screen. It is understood that the output of the system may be in any perceptible form. Such a display device or unit and other input/output devices could implement a program or user interface created by machine-readable means, such as software, permitting the system and user to carry out the user settings and input discussed in this application. 1901, 1903, 1905, 1907, 1919, 1921 and 1923 are connected and able to communicate communications, transmissions and instructions via system bus(ses) 1975. Storage media and/or hard disk recorder and/or cloud storage port or connection device 1905 is capable of providing mass storage for the system, and may be a computer-readable medium, may be a connected mass storage device (e.g., flash drive or other drive connected to a U.S.B. port or Wi-Fi) may use back-end (with or without middle-ware) or cloud storage over a network (e.g., the internet) as either a memory backup for an internal mass storage device or as a primary memory storage means, or may simply be an internal mass storage device, such as a computer hard drive or optical drive. Generally speaking, the system may be implemented as a client/server arrangement, where features of the invention are performed on a remote server, networked to the client and made a client and server by software on both the client computer and server computer.

Input and output devices may deliver their input and receive output by any known means, including, but not limited to, the examples shown as 1917. The input managed and distributed by the system may be any representational aspect or signal or direct impression captured from any sensed or modeled activity, and may be taken or converted as input through any sensor or carrier means known in the art. In addition, directly carried elements (for example a light stream taken by fiber optics from a view of a scene) may be directly managed, manipulated and distributed in whole or in part to enhance output, and whole ambient light information may be taken by a series of sensors dedicated to angles of detection, or an omnidirectional sensor or series of sensors which record direction as well as the presence of photons sensed and/or recorded, and may exclude the need for lenses (or ignore or re-purpose sensors "out of focal plane" for detecting bokeh information or enhancing resolution as focal lengths and apertures are selected), only later to be analyzed and rendered into focal planes or fields of a user's choice through the system. For example, a series of metallic sensor plates that resonate with photons propagating in particular directions would also be capable of being recorded with directional information, in addition to other, more ordinary light data recorded by sensors. While this example is illustrative, it is understood that any form of electromagnetism, compression wave or other sensory phenomenon may include such sensory, directional and 3D locational information, which may also be made possible by multiple locations of sensing, preferably, in a similar or measurably related, if not identical, time frame. The system may condition, select all or part of, alter and/or generate composites from all or part of such direct or analog image transmissions, and may combine them with other forms of image data, such as digital image files, if such direct or data encoded sources are used. Specialized sensors for detecting the presence of interference or resonance of radiation of any type, and imaging the sources or capturing the forces applied based on the known characteristics of waves and electromagnetic radiation in particular, may also be included for input/output devices.

While the illustrated system example 1900 may be helpful to understand the implementation of aspects of the invention, it is understood that any form of computer system may be used—for example, a simpler computer system containing just a processor for executing instructions from a memory or transmission source. The aspects or features set forth may be implemented with, and in any combination of, digital electronic circuitry, hardware, software, firmware, or in analog or direct (such as light-based or analog electronic or magnetic or direct transmission, without translation and the attendant degradation, of the image medium) circuitry or associational storage and transmission, as occurs in an organic brain of a living animal, any of which may be aided with external detail or aspect enhancing media from external hardware and software, optionally, by networked connection, such as by LAN, WAN or the many connections forming the internet. The system can be embodied in a tangibly-stored computer program, as by a machine-readable medium and propagated signal, for execution by a programmable processor. The method steps of the embodiments of the present invention may be performed by such a programmable processor, executing a program of instructions, operating on input and output, and generating output. A computer program includes instructions for a computer to carry out a particular activity to bring about a particular result, and may be written in any programming language, including compiled and uncompiled and interpreted languages and machine language, and can be deployed in any form, including a complete program, module, component, subroutine, or other suitable routine for a computer program.

It should be noted that, in several embodiments of the present invention, it has been stated to be preferable to target leading, outer structures of a target. This serves at least two functions. First, the superposed result will intensify along a path that enters further into the target, rather than exiting the target, at least initially. Second, the Treatment of diseased living tissues may be cut-off from blood supply and metastasis by creating a "dead ring" of encapsulating, ionized tissue. Other patterns, aside from converging and focusing beams and/or waves on the leading structures or volumes of a target may also be used, to otherwise heat, condition and mark the target volume for further identification and actions. For example, patterns which aid in the reabsorption of some targets, such as periodic gaps in heavier dosage designed to "break up" the target mass, may be used. As another example, local regions may be temporarily marked with a pattern of convergent radiation, which may be lower or even a relatively "safe" level, to aid in the proper location of the target for further, ionizing radiation.

The embodiments of the present invention may be combined with radio-sensitizing agents, applied to a target volume (e.g., by injection, or drawing by magnetic field and electromagnetic tagging and/or genetic tagging to match a sequence in malignant cells), or naturally coalescing in a target based on other dynamics (e.g., fluid pathways, colligative forces). Agents that fluoresce or otherwise can be read to indicate radiation pathways through both the target volume and collateral material and media, may also be present systemically, to aid the system in assessing existing radiation beam pathways, and adjusting such pathways to optimize dosage in light of reflection, absorption and refraction patterns, as they are observed. Insertable beacons, which may contain lensing and/or radiation re-routing mirrors or other radiation path-diverting elements, may be placed at or near the target, to allow both the accurate location of the target volume and the focusing of radiation from a more diffuse density of radiation in collateral matter or media, into a more concentrated dosage at the target—or may be placed to allow circumnavigation of critical structures, which thereby avoid radiation dosage. More conventional tagging, such as body surface tagging, may also, or alternatively, be used to locate a previously determined target location. The system may plan for, and verify, oscillating or other movements (e.g., breathing, heartbeat, body roll), and how they proceed in comparison to a target, to more accurately locate the target by using a plurality of cross-compared beacons (e.g., by triangulation, quadrangulation, etc., with correction for outlier movements or oscillations of one or more tags). As discussed in greater detail below, a control system such as that discussed with reference to this figure may be used to control any servo motors, instruments and radiotherapy emission sources set forth in this application for controlling radiotherapy techniques, as well as imaging devices, with programming dictating such execution and/or control, by any known wired or wireless communications and command protocols, and carry out or control any aspects set forth in this application. The control system set forth with reference to this figure may also power any such devices or, alternatively, a separate source of power may supply both the devices and the control system.

In other aspects of the present invention, a target volume may be accelerated toward a source beam as the pulse enters the target volume, thereby increasing the frequency and energy level in the target, while reversing acceleration as the radiation exits. Using a high frequency vibration of the target volume, relative to its collateral material, and a set of sources delivering radiation at the same time and against the same direction as each vibrational acceleration, it is possible to increase the energy level of absorbed radiation, while decreasing it for collateral material and media.

Figure 20:
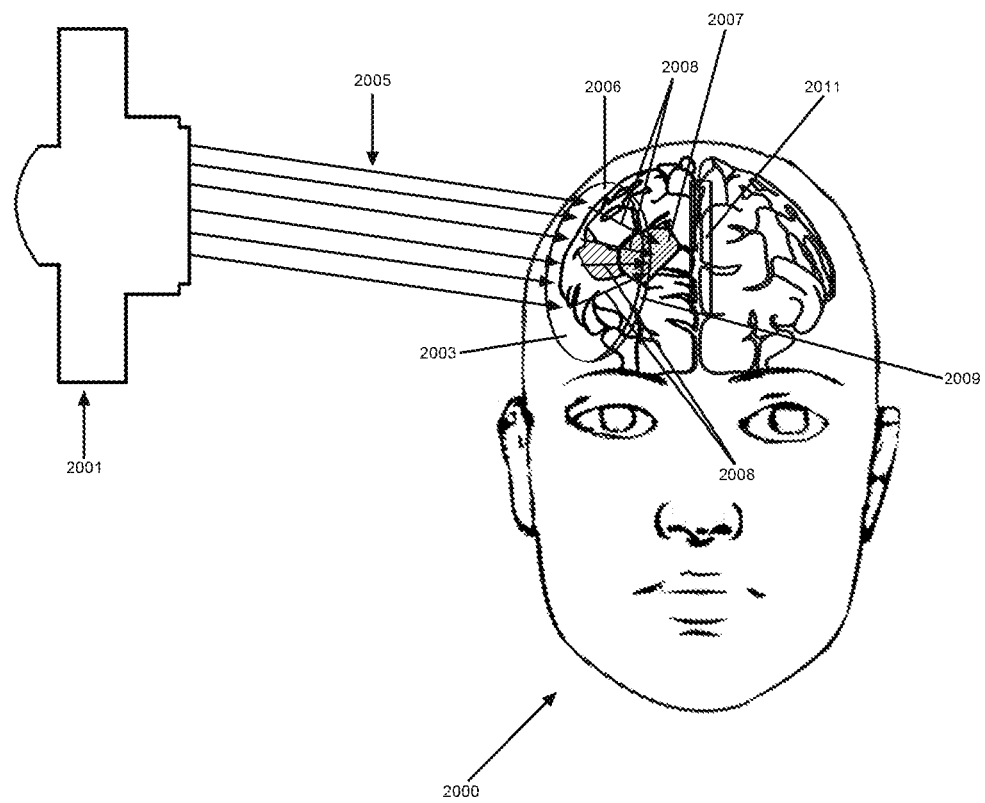
FIG. 20 is a partially cutaway frontal view of a human head, a radiation source and an implantable fluorescent focal device, for use in radiation therapy in accordance with aspects of the present invention.

FIG. 20 is a partially cutaway frontal view of a human head 2000, a radiation source 2001 and an implantable fluorescent focal device 2003, for use in radiation therapy in accordance with aspects of the present invention. As in other aspects of the present invention, an externally-originating beam of radiation 2005 is provided, and aimed generally toward a target mass 2007. However, the fluorescent focal device 2003 is placed in between source 2001 and target mass 2007 and external beam 2005 specifically targets a beam-facing, external, absorptive section 2006, comprising atomic, molecular and/or larger constituent structures capable of absorbing energy from external beam 2005 and, as a result, emitting a different, higher energy or otherwise more tissue-destructive form of radiation, focused toward the target mass 2007. In other words, focal device 2003 fluoresces in response to receiving source beam 2005 and also serves to focus fluoresced beams of radiation 2008, concentrating them on the target mass 2007. Device 2003 may further comprise a radiation-lensing or otherwise radiation-focusing emissive shaped surface 2009, aiding in achieving that focus for the emitted radiation 2008. In addition, a variably implantable shield 2011 may be placed on a side opposing fluorescent focal device 2003, specifically positioned to absorb the fluorescent beams 2008. In some embodiments, which are preferred, device 2003 creates a limited, controlled-width range of beams, and the beams emit a form of localized or locally absorbed radiation. As a result, the size of both the device 2003 and the shield 2011 may be limited in at least one dimension, greatly reducing their necessary, complementary profile, and greatly decreasing the adverse impact (if any) of their implantation.

In some preferred embodiments, external source beam 2005 is of a relatively harmless form of radiation, relative to human tissue (and its genetic material). However, the emitted beams 2008 from fluorescent device 2003 are preferably tissue-ionizing. To achieve this, multi-photon absorption within the structures of device 2003, and/or magnetic actuation of device 2003 may be used. Alternatively, a less harmful, albeit somewhat ionizing form of radiation, may be used as the external beam of radiation 2005. In other embodiments, a radiation source may be included within device 2003, and may be variably shielded by external (including remote control) actuation of a movable shield or interlaceable matrix (not pictured) that may variably withhold the radiation and/or convert it to a harmless form, and, in some embodiments, variably shield that radiation in specified emissive directions (e.g., by variably-pivotable shield louver(s) (also not pictured).

Figure 21:
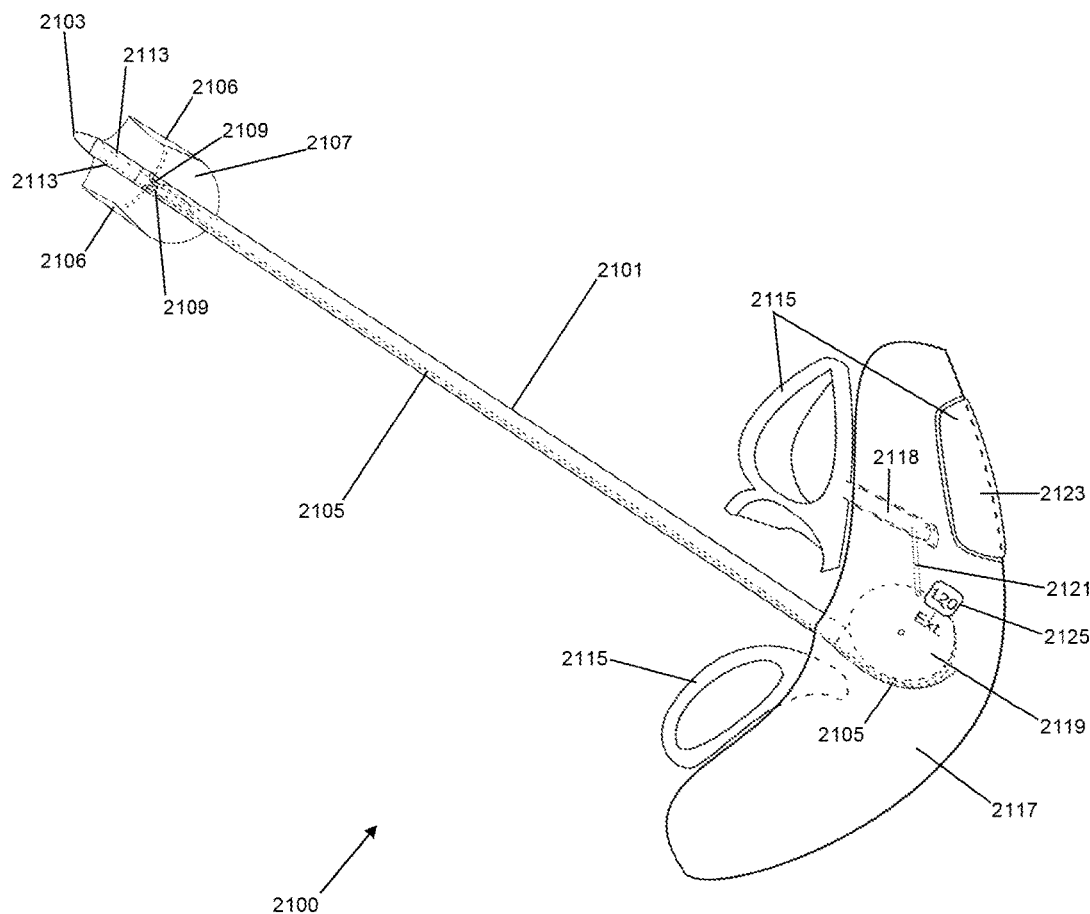
FIG. 21 is a perspective view of an exemplary endoscopic radiation focal and shielding instrument, in accordance with aspects of the present invention.

FIG. 21 is a perspective view of an exemplary endoscopic radiation focal and shielding instrument 2100, in accordance with aspects of the present invention. Focal instrument 2100 comprises a main cannula 2101. Cannula 2101 is insertable into a human or other animal patient's body with the aid of a rounded, tapered insertion-facilitating tip 2103, which may penetrate and be inserted through skin, muscular walls, viscera and other organs and layers of tissue—in some embodiments, with the aid of prior incisions through which tip 2103 may then be threaded. Within cannula 2101 is a push-band 2105, with a high tensile rigidity—in other words, it is relatively inelastic, incompressible and unstretchable along its length, permitting pushing movements to be translated directly into actuation movements of a device attached to its end. However, band 2105 is relatively flexible, and able to turn and curve along its length through channels and around walls within cannula 2101 and instrument 2100 in general. Examples of materials with these properties when in the form of band 2105 include various plastics and natural fibers, such as cellulose, known in the art. Band 2105 splits at the end nearest to tip 2103, and its split end is attached to distal edges 2106 of a device at the same end of cannula 2101 as tip 2103—namely, an extending, curving shield, mirror, lens or other curved sheet (or set of sheets) 2107. When the length of band 2105 is pushed toward tip 2103, band 2105 is not compressed, but turns in channels 2109 within cannula 2101, which translate the motion of the ends 2111 attached to edges 2106 into pathways perpendicular to the length of cannula 2101, and sheet 2107 is extended (as pictured). Due to a natural tendency to curve of sheet 2107, sheet 2107 takes on a conformation when extended presenting as a concave mirror or other focal lens, or enveloping shield (facing the viewer and upper-left-corner, in the perspective of the figure. Conversely, when band 2105 is retracted, focal sheet 2107 is retracted and folded substantially into the body of cannula 2101 (within storage pockets 2113). Sheet 2107 may comprise folding and elastic, force-biased materials that encourage that folding and storage, when band 2105 is so retracted.

Driving the pushing or pulling of band 2105 (to cause the extension or retraction, respectively, of sheet 2107) are manual controls 2115, attached to a handgrip 2117, itself attached to the end of cannula 2101 opposite tip 2103. In some embodiments, controls 2115 may be electronic, and actuate band retraction and extension via servo/motors wired or otherwise in communication with controls 2115. However, preferably, at least some of controls 2115 are manual, as pictured, to preserve actuation feel, and attached physical connections, such (such as exemplary push rod 2118 connected to the index and second-finger-actuated manual control loop, at the top) to a lever or wheel (such as exemplary push wheel 2119, via connector 2121), to cause band 2105, connected to the outer edge of lever or wheel 2119, to be correspondingly pushed or retracted in channels within cannula 2101. The lowest control 2115 (which may control another feature of device 2100, not pictured), by contrast, is pinky and/or ring finger actuated, and cannula 2101 is preferably held between the second and ring fingers, as the user's hand grips handle 2117.

In a preferred method, a surgeon facilitates radiotherapy or radiosurgery using instrument 2101 by: retracting sheet 2107 (or ensuring that it is retracted) into pockets 2113; creating entry incision(s) for a pathway to the far side (opposing the direction from which radiation will be sent) of a radiation treatment target, preferably, at least partially surrounding said treatment target, and focusing radiation onto a treatment target while shielding tissues neighboring the treatment target from radiation when sheet 2107 is later extended; substantially so extending sheet 2107; dosing sheet 2107, the resulting mirror lens it forms, and the treatment target with radiation, while shielding neighboring tissues from the radiation. As will be explained in greater detail below, in some methods of the present invention, the surgeon may also cauterize tissues as he or she is inserting instrument 2100, or extending sheet 2107. The steps of the methods discussed above may be carried out in a wide variety of alternative orders, and the listed order is exemplary only.

In some embodiments, the leading edges 2106 of sheet 2107 are electrically-powered cauterizing devices, wired to a power source (e.g., through a wire embedded in band 2105). In such embodiments, a surgeon using cannula 2101 may cauterize and penetrate tissue blocking the path of sheet 2107 as it is extended, for example, using a cautery-actuating thumb button 2123, electronically controlling the cauteries. A power source and control system for actuating the cauteries, and other controls, if electronically controlled in the given embodiment, may be resident within instrument 2101 and wired to the actuators they control and power, or may be resident elsewhere but connected to or otherwise able to transmit power and communications to those controls and actuators which they control.

Although the example of an instrument administered focal mirror or other lens is shown, it should be understood that this is exemplary, and a separate (or detachable focal mirror may be positioned and or implanted as discussed in reference to this figure. Similarly, a fixed, rather than collapsible mirror or focal lens may be used, in some embodiments.

To guide a surgeon using device 2100, an extension indicator, such as extension degree indicating window 2125 may be included. The rotational degrees surrounding a treatment target that is the focus of mirror or lens 2107 (and therefore, the degree of extension of mirror or lens 2107) may then be indicated to the surgeon, as he or she extends it. This indicator may be manually driven, by labels on wheel 2119, visible through window 2125. Alternatively, window 2125 may be a control system-actuable and powered (e.g., LCD) display.

Figure 22:
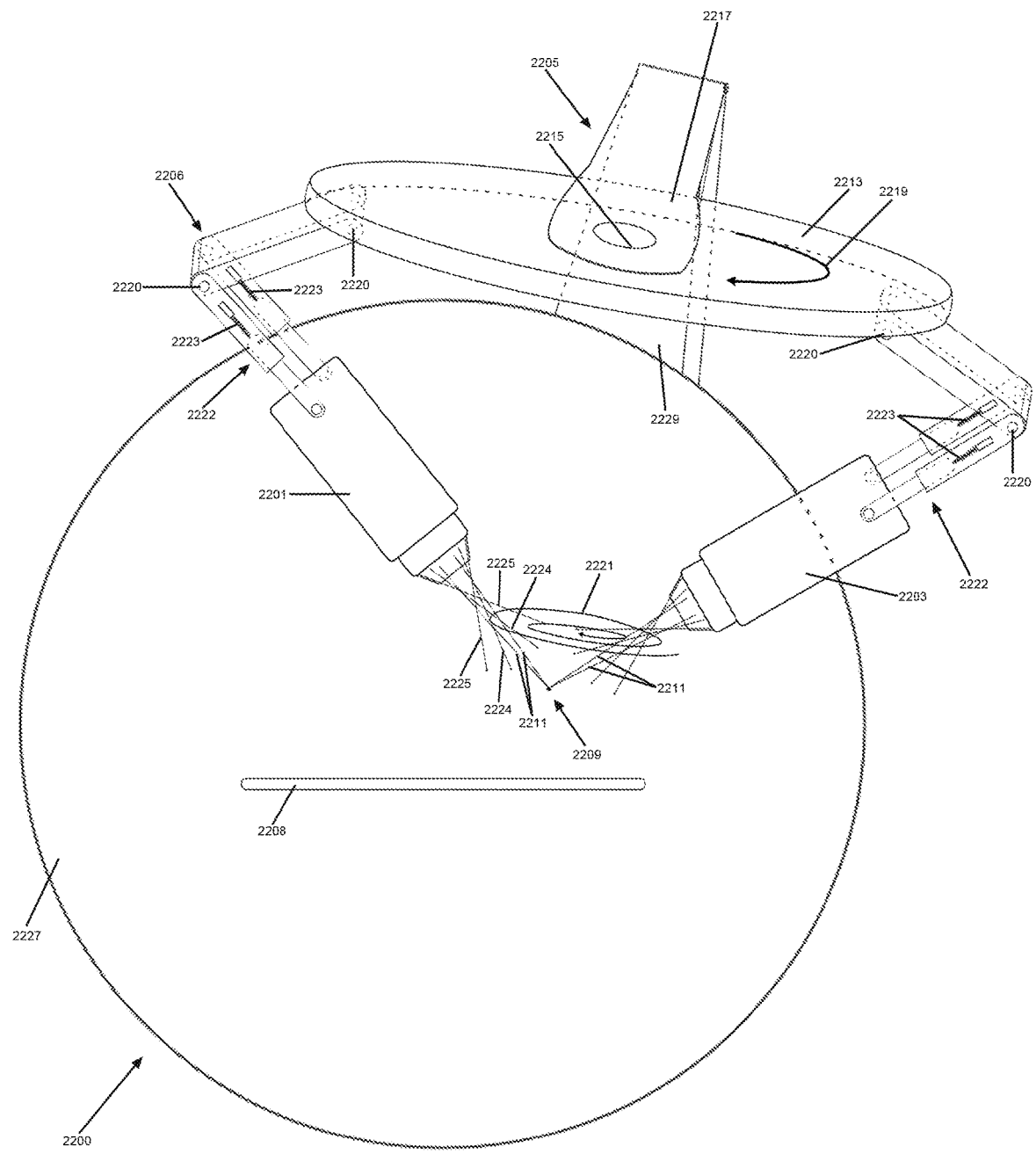
FIG. 22 is a perspective drawing depicting a new radiotherapy machine with multiple, simultaneous radiation sources.

FIG. 22 is a perspective drawing depicting a new radiotherapy machine 2200 with multiple, simultaneous radiation sources 2201 and 2203. Each radiation source, 2201 and 2203 may be positioned at a wide variety of radiation emission angles by a computer system-actuable gantry 2205 (comprising a set of adjustable, actuable arms 2206 and 2207) to treat a target mass inside a human or other animal subject (not pictured) laying on a flat bed 2208. Furthermore, sources 2201 and 2203 may be put in motion during such treatment, while remaining trained on the target mass (e.g., at a point 2209) preventing the prolonged irradiation of tissues collateral to the treatment target (through which, radiation beams, such as examples 2211, pass to reach point 2209). Gantry 2205 is able to position sources 2201 and 2203 at opposing angles from a line perpendicular to the surface of the human or animal subject (as pictured). In a preferred embodiment, the opposing nature of the positions of sources 2201 and 2203 are maintained, as they are put in motion as discussed above. Also in a preferred embodiment, sources 2201 and 2203 are placed in continuous motion by a rotating rig 2213 to which they are attached, and which is rotated about an axel 2215 by a computer-system controlled motor within a main supporting arm 2217 (which itself may be position adjusted by control system actuable motors). For example, in one exemplary embodiment, rig 2213 rotates about axel 2215 during radiation treatment in a clockwise direction (when viewed from above, as pictured) as illustrated by rotational motion arrow 2219. In addition, each source 2201 and 2203 may be, simultaneously with this rotational motion, raised to increasingly acute angles with the parallel line from the surface of the subject, by control system actuated servo motors within arms 2206 and 2207, controlling the angle of hinges 2220, and linear actuators 2223 controlling the control system-variable length of arm sections 2222. Correspondingly, emitted beams 2211 from one of the sources (namely, 2201) are swept across a spiral path about exemplary spiral pattern 2221 at the outer surface of the human or animal subject. The emitted beams from the other source (2203) is also swept across a spiral path, preferably different from spiral path pattern 2221, and, even more preferably, exactly centered within the spaces between spiral path 2221, as pictured. An example of such an overlapping pattern is shown below, in FIG. 23, as exemplary overlapping pattern pair 2301. To accomplish this, the opposing angle of source 2203 is not an exact mirror image of the angle of source 2201. But both paths, 2221 and the corresponding path of source 2203, are constantly trained at the target mass (e.g., at point 2209). In an even more preferred embodiment, the spiral paths are adjusted and morphed to optimize the distribution of radiation to the treatment target, and throughout, collateral non-treatment subject tissues. This adjustment can be made in real time, based on live imaging of the treatment target and other subject tissues.

In addition to the varying, opposing treatment angles of sources 2201 and 2203, each source 2201 and 2203 may further comprise multiple beams of radiation 2211, emitted from opposing angles and intersecting at the treatment target (e.g., point 2209) as pictured. Preferably, the position and angle of the multiple beams may also be varied, leading to the ability to select intersection points at different distances from the source 2201 or 2203. For example, alternate beam positions 2224 and 2225 may be selected and control-system-mandated. By transitioning to such paths, and controlling gantry 2205 to maintain the intersection of the emitted beams at the treatment target (e.g. 2209), the dosage to collateral tissues may be even more greatly varied, and spread out across them, while maintaining treatment of the target.

In addition, the control system may both rotate main gantry wheel 2227 and body length position adjusting arm 2229 (which the control system may shift fore and aft along bed 2208) to distribute the dosage about through wide variety of subject surfaces, anywhere all the way around the subject, and administer the spiral dosages in a smeared out pathway, wrapped and bent around the subject.

Due to the differing positions, rotational velocity and movements of sources 2201 and 2203, and different collateral matter through which radiation generated from the sources must travel, the control system may determine the relative positions of each source from the target, and map all collateral matter, along a function describing the beams' path, and adjust the period, frequency, or any other attribute of beams that they each generate, to carry out constructive superposition at the target throughout treatment in accordance with aspects of the present invention set forth in this application. As with other aspects discussed above, a longer beam path to target, due to a greater distance of a source or greater or more instances of refraction through collateral matter in a beam path, may be determined by the control system, may require advancing the period as the beam is emitted, to optimize constructive interference at the target. The system may seek and exploit paths with greatly differing distances in this way, to decrease incidental constructive interference, and increase protection (by destructive interference) in collateral objects through which the beam paths pass prior to reaching the target. Differences in the birefringence of the collateral material through which the different beams pass may also be determined and applied in planning the period and other wave attributes of each beam upon emission, projecting and causing them to constructively interfere upon arrival at the target site, but not at other, earlier and later, points in time.

Radiotherapy machine 2200 may be used with sources implementing other aspects of the invention set forth in this application. For example, beams from source 2201 may be generated that have the same period and frequency, or a harmonic or otherwise constructively-building frequency, when they intersect at the above-stated intersection points. And any beam from source 2201 and source 2203 also may be generated that have the same period and frequency, or a harmonic or otherwise constructively-building frequency, when they intersect at the above-stated intersection points.

But machine 2200 may also be used with more conventional radiation therapy sources and techniques, not involving the intersection of beams at a target, with their separation within collateral tissues. In another embodiment, one source 2201 does not simultaneously treat the same point as source 2203, and their respective beams need not intersect with one another. Instead, a source first treating the target point charges the materials with its radiation beams (some of which are absorbed within atoms of the target mass, e.g., exciting electrons within DNA to higher-energy orbitals. While still charged, the second source then treats the same point, leading to additional energy absorption, breaking of bonds, and greater destruction of the target mass. In this way, dosage to collateral matter can be even more greatly distributed.

Figure 23:
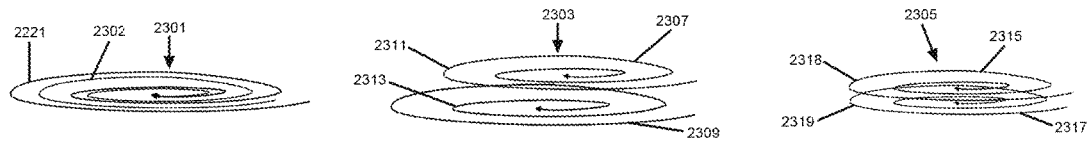
FIG. 23 depicts a series of radiation beam pattern pairs emanating from sources discussed in FIG. 22.

FIG. 23 depicts a series of radiation beam pattern pairs, 2301, 2303 and 2305, emanating from sources 2201 and 2203, discussed above. It is to be understood that, as with pattern 2221, discussed above, these patterns occur at or about the surface of the human or animal subject (pair 2301 and 2303) or within the subject's body, but not as far down as the target point (pair 2305). First, in pair 2301, as discussed above, a pattern from source 2201 at or about the surface of the subject is pictured (also pictured in the greater context of a radiotherapy machine in FIG. 22, above, as spiral pattern 2221.) A second spiral, 2302, is also pictured, spaces between pattern path 2221. As both patterns descend and converge toward a target, however, they merge and, due to overlapping constructively interfering frequencies, periods, polarity or other attributes, form a united waveform of much higher energy density at the treatment target. In an embodiment creating pattern pair 2301, each source preferably has an angle relative to a line perpendicular from the subject's outer surface permitting the nesting of spiral 2302 within the interstitial space of pattern 2221 until each pattern reaches the treatment target.

Beam pattern pair 2303 illustrates additional features, comprising destructive interference at a point in time prior to beams from the two sources converging. The top pattern, 2307, describes a pattern above the subject drawn by source 2201, which is positioned at an angle more acute to the perpendicular line from the surface of the subject than source 2203. The lower pattern, 2309, is drawn by source 2203, out wider from the subject than source 2201, at the surface of the subject. Due to its more oblique treatment angle, pattern 2309 is wider and descends more slowly than pattern 2307. But pattern 2309 also converges at a greater rate than pattern 2307. Thus, at the instant pictured, the outer edge sweep 2311 of pattern 2307 may abut an inner sweep 2313 of pattern 2309. If those abutting regions are made, by a control system planning the period, frequency, polarity and other radiation wave attributes of each pattern, to destructively interfere at the instant shown, protection will then occur at the instant pictured. At a later interval within a treatment target, however, due to the greater rate of convergence and slower rate of descent of pattern 2309, the two patterns (then depicted as 2315 and 2317) are then overlapping at constructively related regions, as they converge—again by a control system planning the period, frequency, polarity and other radiation wave attributes of each pattern, causing outer region 2318 to constructively interfere with region 2319.

The control systems discussed in FIGS. 21-23 may be a computer system such as that set forth earlier in this application, with reference to FIG. 19.

Figure 24:
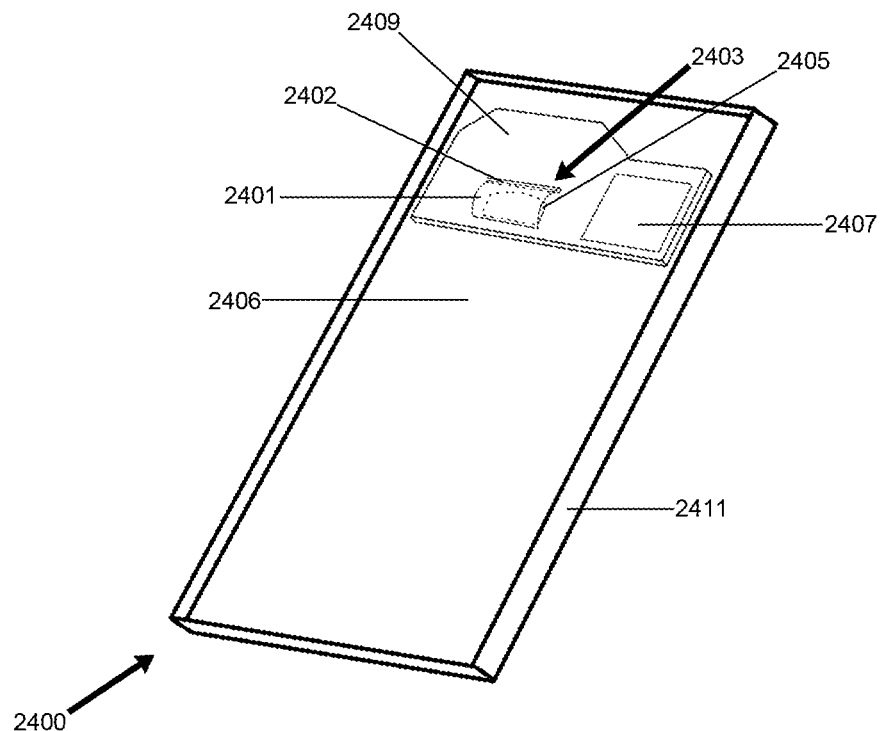
FIG. 24 is a perspective drawing, depicting aspects of the invention applied in a handheld wireless communications device.

FIG. 24 is a perspective drawing, depicting aspects of the invention applied in a handheld wireless communications device 2400. As with the instrument and method set forth above, in reference to FIG. 21, device 2400 comprises at least one extendable and retractable sheet 2401, which forms a concave mirror or other focal lens, or enveloping shield when extended (as pictured). Also as with the sheets described in reference to FIG. 21, and by the same encompassed features, sheet 2401 envelopes more greatly, and becomes more concave, the more it is extended from a stowage bay 2402 comprised in an actuator—in this instance, shielding and focusing actuator 2403 (in which sheet 2401 may be furled, for example, around a rotary motor to which it is attached). However, unlike the embodiment set forth in FIG. 21, in this instance, sheet 2401 does not extend to cover a treatment target. Instead, sheet 2401 is sized and curved to envelope a wireless communications broadcasting sub-device 2405, when sheet 2401 is extended from bay 2402. As pictured, broadcasting device 2405 is comprised in communications device 2400. Communications device 2400 may be any portable communications device that may be held in close proximity to a human or other animal. For example, communications device 2400 may be a smartphone, personal digital assistant, tablet, or other personal computer. Broadcasting device 2405 may be a WIFI or other antenna, other wireless communications gear or any device emitting any form of radiation, or potentially emitting any form of radiation. The broad side 2406 of communications device 2400 that faces the viewer of the figure is the side of communications device 2400 that faces a user of the device, during normal usage. A screen or other GUI, along with a mounting bracket, may be overlaid onto side 2406, when the complete device is assembled.

Thus, when sheet 2401 is extended from bay 2402, enveloping the side of broadcasting device 2405 that faces a user of device 2400, it serves to: (1) focus ambient electromagnetic radiation received from the other side (facing into the page) of device 2400 onto broadcasting sub-device 2405; (2) reflect outbound electromagnetic radiation toward another device(s) with which device 2400 is communicating, and (3) shield the user from electromagnetic radiation from device 2400 and other sources. Depending on the degree of extension, sheet 2401 will undertake more curved (when fully extended) and more flat (when closer to fully retracted) shapes. Thus, a control system in communication with and controlling sheet 2401 and actuator 2403—such as control system 2407—can select from a variety of altered outbound and incoming angles of shielding and reflection, to better focus, receive and send electromagnetic signals from sub-device 2405, and actuate actuator 2403 to create those angles of shielding and reflection, depending on conditions sensed by the control system.

For example, if ambient radiation sensed by device 2400 is of a sufficient strength, reception of electromagnetic radiation from all sides of broadcasting sub-device 2405 may not be required to establish an adequate local network connection for device 2400 and, as such, the control system may fully extend sheet 2401, to maximally protect a user on the user's side of device 2400. If, however, the signal later decreases in strength, or a wireless connection is otherwise lost, decreased in quality or moves, the control system can command actuator 2403 to retract, completely or to varying degrees, to select angles of reflection and focus that maximize reception of the electromagnetic signals. Control system 2407 may be any suitable control system, such as the control system set forth in reference to FIG. 19, above, and may communicate with and/or partially reside on remotely connected hardware. Sheet 2401 may comprise of or be lined with a fine mesh or other layer of copper or any other materials known in the art to shield electromagnetic radiation. Sheet 2401 may also be lined with a layer of any electromagnetic reflective material known in the art. While such details have been eliminated for clarity of visual presentation, it should be understood that any part of communications device 2400 may be connected to any other part of communications device 2400, for example, by wired or wireless interconnections. Similarly, any part of communications device 2400 may be physically connected to any other part by any connecting devices known in the art (e.g., solder, screws, and intermediate brackets, such as bracket 2409, shown mounting control system 2407 and broadcasting sub-device 2405, and connecting them to outer housing section 2411).

Figure 25:
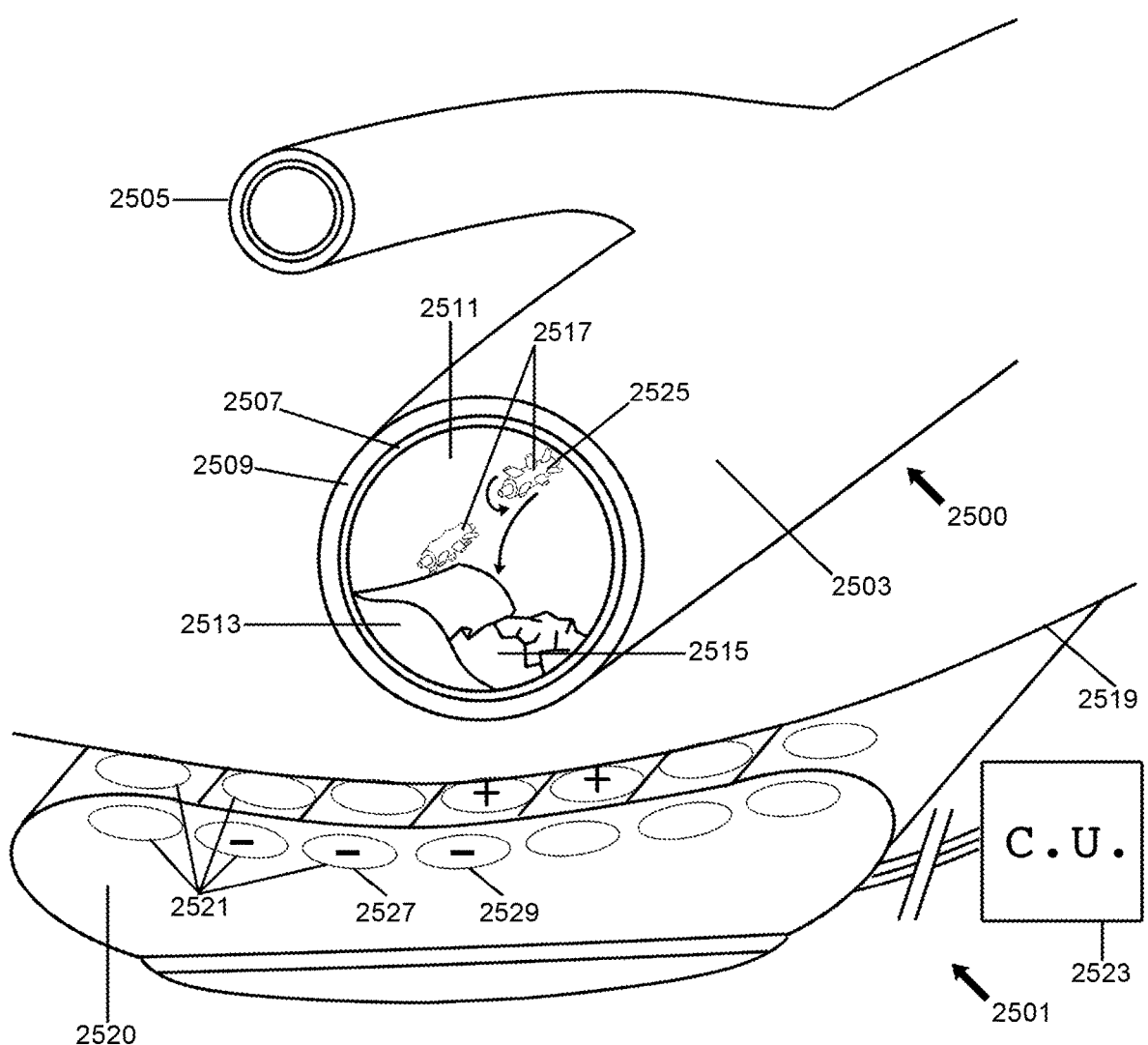
FIG. 25 is a perspective drawing of another exemplary treatment target—namely, a mammalian artery with cardiovascular disease—under treatment by small scale devices and remote actuation systems, in accordance with aspects of the present invention.

FIG. 25 is a perspective drawing of another exemplary treatment target—namely, a mammalian artery 2500 exhibiting cardiovascular disease—under treatment by small scale devices, such as the devices discussed in reference to FIG. 26, below, and a remote actuation system 2501 in accordance with aspects of the present invention. Artery 2500 comprises at least two branches, including a larger, main branch 2503, and a capillary branch 2505. Both branch 2503 and 2505 are pictured cross sectioned at a location facing a viewer of the figure, and coinciding with a diseased section of the artery, to reveal their anatomy and to illustrate aspects of the invention more completely. Main branch 2503 comprises several usual anatomical features of healthy arteries, including different layers of smooth muscle and collagen, such as the internal tunica intima layer 2507, the and a surrounding tunica media layer 2509. Within main branch 2503, there is a central lumen 2511, which is a channel for the transportation of blood and its components, as well as particular small-scale devices injected into it, as set forth in the present application. Due to any of several possible factors, such as a genetic predisposition to high bad cholesterol and a new fat-heavy, high-sugar, low fiber, and low magnesium Western diet for which humans have not yet evolved, main branch 2503 exhibits cardiovascular disease, including an arterial plaque 2513, a neighboring blood clot 2515, abutting plaque 2513, and a general narrowing and calcification and decreased elasticity ("hardening" of the artery.) This condition is a leading cause of death, worldwide, including sudden death with no prior symptoms, because it can lead to a cascading effect in which a blood clot rapidly expands and closes a vital artery. While this type of cardiovascular disease takes many years to become life-threatening, it begins surprisingly early—in childhood for males, who lack the beneficial protective effects of a high estrogen component in the bloodstream. Physicians may administer blood-thinners, such as coumadin, for patients with a history of blockages such as this, and blood-thinners may contribute to artery hardening. Thus, because they are each life threatening, interrelated conditions, both plaque 2513 and clot 2515 may each, and/or individually, be considered a treatment target for aspects of the present invention. It should be understood, however, that these targets, and the anatomical structure depicted, are exemplary only, and that aspects of the invention may be applied equally to a wide variety of additional treatment targets, such as tumors, foreign bodies and pathogens, in lymph, within other tissues, or in any interstitial fluid. Rather, the specific example provided herein is one example of the type of context and treatment targets in which the invention may be applied.

In accordance with aspects of the present invention, remotely-applied treatments including the administration of a plurality of small-scaled devices, such as the examples shown as 2517 within lumen 2511, are provided. As set forth elsewhere in this application, in relation to other remotely-actuated small-scale treatment devices, devices 2517 may be injected directly into the lumen, if they are made on a small enough scale to be provided by hypodermic injection (and/or a new form of hypodermic needle configured to pass remotely-administered small-scale machines, as set forth elsewhere in this application, is used). Also as with other small-scale machines set forth in the present invention, devices 2517 comprise different charged regions and/or dipoles, allowing an external electromagnetic or electrostatic control system, such as the example set forth as 2519, to control the location, orientation, and overall movement of devices 2517, as well as the actuation of particular sub-devices comprised in devices 2517.

To remotely control devices 2517, from a location external to artery 2500 (and surrounding tissue 2519) an external treatment head 2520 is provided. Treatment head 2520 is configured to be externally placed (for example, on the outer surface of a patient's skin) with individually modifiable electrostatic charges and/or dipoles, for example, at charge application regions 2521. By individually addressing and modifying the charges and dipoles at each of regions 2521, an attached control system 2523, such as and which may be the control systems set forth in reference to FIG. 19, above and in other figures setting forth exemplary control systems in the present application, may create a wide variety of different electromagnetic and electrostatic fields. More specifically, an electronic power source within control system 2523 may be applied through separate wires to chargeable regions within head 2529, as will set forth in greater detail below. For ease of understanding and viewing, each of these possible configurations of wires, chargeable region ferromagnetic components, and software aspects for driving magnetic fields will not be covered in detail again in this part of the application. These fields, although applied from outside of the treatment targets and blood vessel 2500, penetrate those structures, creating a variable magnetic field within the lumen 2511 which individually directs both the orientation and movement of each of devices 2517, and each of their sub-devices. The control system may do so by creating magnetic or electrostatic fields which interact specifically with charges and dipoles within devices 2517 and within their sub-devices. As a result, the control system 2523 may cause devices 2517 to rotate and move toward and into plaque 2513 or clot 2515, causing them to break up, dissolve or compress. For example, one of devices 2517, namely, device 2525, is shown at a position upstream of bloodflow within artery 2500, drifting in an orientation which is not ideal for treatment. This may be desirable in areas not in need of treatment, because a side of device 2525 without structures for the treatment of plaques or clots (e.g, smooth, or lightly-ridged surface) is less likely to collide with and damage healthier arterial structures in this orientation. However, as the devices 2517 approach the treatment targets, the control system begins to administer a negative charge, and, thereby, attractive magnetic or electrostatic field, to regions near the treatment targets, such as regions 2527 and 2529. This negative charge pulls a positively charged region of each device 2517 toward it, orienting it toward the treatment targets and driving a modified motion vector for each of the devices into the surface of the plaque or clot. Control system 2523 may also apply opposite charges and dipoles to other regions, to encourage or strengthen the orientation and drive additional, more localized electromagnetic fields, and the actuation of specific sub-devices comprised in devices 2517.

Some exemplary sub-devices of small-scale machines such as 2517, and some exemplary specific functions, will be set forth in greater detail below, in reference to FIG. 26. Of course, the exact shapes and surface features shown for machines 2517 are merely exemplary of the wide range of possible shapes, sizes and actuable sub-devices which may be used while carrying out aspects of the present invention, as will be readily apparent to those of ordinary skill in the art. For example, in some embodiments, rather than having a "spiny" appearance, such machines may instead include blades or surface ridges with a different profile. In some embodiments, such spines, blades and/or ridges may be provided on only one side of machines 2517, and the control system may prevent or cause abrasion on medical treatment targets by directing the orientation of that side toward, or away from, a biological target or tissue, as the machine passes by such a target or tissue within a bodily fluid (e.g., blood or lymph into which it was introduced.)

Figure 26:
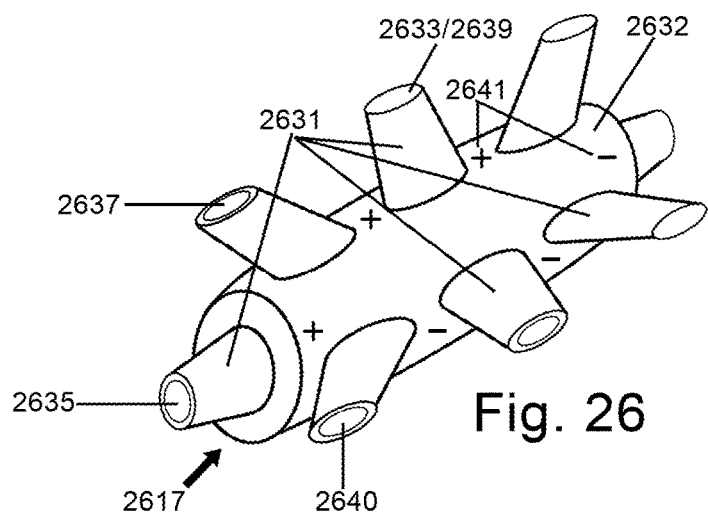
FIG. 26 is a perspective drawing of an exemplary small scale device for injection within a treatment target, such as the treatment target set forth above, in FIG. 25.

FIG. 26 is a perspective drawing of an exemplary small scale device 2617, configured for injection within a treatment target, such as the treatment target set forth above, in FIG. 25. Because exemplary device 2617 is shown at a larger scale than devices 2517, in FIG. 25, several exemplary features, such as dub-devices, may be explored in greater detail. For example, in the figure, a series of treatment probes, such as the examples shown as 2631, radiating upward and sideways from a main body 2632 of device 2617, may be seen. Each of probes 2631 may comprise edged projections 2633, for colliding with, slicing into, and breaking up treatment targets with which they collide. In addition, each of probes 2631 may contain deployable medications or other agents, for example, within a central storage void 2635. In some embodiments, central storage void 2635, alternatively or in addition, holds and delivers an abrasive particle(s). For example, in some embodiments, the control-system actuates a release door and/or pump, releasing such abrasive particles when the probe is touching or near by a treatment target. In some embodiments, such release of such particle(s), medications and/or agents may be mediated by contact with a treatment target, and the resulting colligative or inter-molecular forces. In some embodiments, the surrounding substance of probes 2631 comprise an inert or relatively inert material, which will not react with or decompose when driven into a treatment target. In those embodiments, preferably an opening 2637, at or near the tip 2639 of each probe 2631, allows the deployment of medication, particle(s) and/or agents from voids 2635, and into the treatment target. This deployment may be mediated by the breaking open or other degradation of an encapsulating plug 2640, which otherwise holds in the medication or other agent.

In other embodiments, probes 2631 and/or plugs 2640 may comprise a substance that reacts with a treatment target, such as an unstable polymer, acid, base, volatile chemical, or another reactive chemical, conjugated with the medication or agent. In still other embodiments, the medication or agent may be held facing outward, by such a polymer placed at the inside of the sub-device. In those instances, targeting reaction at the treatment site is controlled by lower probabilities of collision with healthy tissue, when the probes 2631 are not being actively driven into a target. In these embodiments, some reaction with healthy tissue will occur, but to a far lesser degree than with the treatment target.

To encourage probes 2631 to face and be driven into a treatment target, the main body 2632 has regional charges or dipoles, such as the examples shown as 2641, allowing a magnetic field to alter the exact orientation and movement of device 2617, and its sub-devices. In some embodiments, at least two different dipole(s) are included within such a probe(s). Preferably, each such dipole is along a different three-dimensional axis from each other dipole, and separately addressable by the control system in accordance with the methods for remotely addressing multiple dipoles of small-scale devices set forth in this application. Even more preferably, at least three different dipoles, oriented along three different three-dimensional axes, are included within such a probe(s). Similar dipoles or charges may be placed in specific regions on the sub-devices as well (for example, to drive a pinching together of neighboring probes 2631, pinching or cutting into material of the treatment target). In other embodiments, such sub-devices may take on a different (e.g., pinching together) conformation when heated and, while devices such as 2617 are oriented by a magnetic or electrostatic field to face a treatment target, radiation emanating from direction of the treatment target (in accordance with any of the radiation therapy techniques set forth in this application) may cause that heating and resulting actuation of the sub-devices. Although the example of a cutting, probing or pinching subdevice is provided, it should be readily understood that these specific types of devices are exemplary only, and a wide variety of additional sub-devices may be, alternatively and addition, be used in accordance with the techniques set forth in this application. For example, cutting or grinding wheels, or shovels, or picks, or blades or brushes, anchors, extendable sections, or doors and protective smooth capsules, each with separately addressable and driveable dipoles or different actuable conformations upon heating or electrostatic charging, may instead or in addition, be used in any particular device. In some embodiments, the abrasive particles and/or probes used to erode the surface of a treatment target generate small biological particles as a product, debrided from the treatment target. Preferably, those biological particles are of a size on the microscale. Even more Preferably, those biological particles are of a size on the nanoscale.

Although the example of a small-scale probe or other device is shown in several examples of the invention set forth in this application, it should be understood that, in some embodiments, a medical reagent, such as a chemical, pharmaceutical or sub-atomic particle, electromagnetic particle or photon, may instead, or in addition, be used. For example, in some embodiments, an electrostatically charged atom, drug, or molecule may be directed and oriented by the control system, in accordance with the methods set forth herein for directing and orienting small-scale devices. In some embodiments, such molecules are small-scale molecules (e.g., below 1 mm, or below 10 nm, or below 5 nm, or below 2 nm or below 1 nm). In some such embodiments, such particles are small scale particle(s) (e.g., below 1 mm, or below 10 nm, or below 5 nm, or below 2 nm or below 1 nm). In some embodiments, the control system may target such medical reagents with electromagnetic radiation from an emitter, heating or otherwise energizing the reagent above a required reaction energy for creating a desired reaction between the medical reagent and the treatment target. Preferably, such heating or other energizing takes place and is maintained as the medical reagent contacts the treatment target. In some embodiments, multiple beams of radiation, emanating from the same side of a patient (e.g., the treatment side, as defined in this application) are used to so heat or otherwise energize such a reagent. In some embodiments, any of the techniques set forth in this application related to treatment and protection using multiple overlapping beams of radiation may be used to so heat or otherwise energize such a reagent, or any of the microscale and/or nanoscale devices set forth herein.

I claim:

1. A medical reagent application system, comprising:
a control system comprising computer hardware and software, remote from a medical reagent application target, wherein said hardware comprises:
a guidance system comprising a control system actuable magnet, the guidance system being configured to cause a magnetic field to drive a three-dimensional acceleration of a medical reagent into said medical reagent application target along an at least partially pre-planned path based on varying three-dimensional contours of a surface area of said medical reagent application target; and
a radiation emitter, configured to increase an energy level of said medical reagent above predetermined energy level within said medical reagent application target.

2. The medical reagent application system of claim 1, wherein said medical reagent comprises a pharmaceutical.

3. The medical reagent application system of claim 1, wherein said medical reagent comprises a small molecule drug, with a size below 10 nanometers.

4. The medical reagent application system of claim 1, wherein said medical reagent comprises a small molecule drug, with a size below 5 nanometers.

5. The medical reagent application system of claim 1, wherein said medical reagent comprises a small molecule drug, with a size below 2 nanometers.

6. The medical reagent application system of claim 1, wherein said medical reagent comprises a small molecule drug, with a size below 1 nanometer.

7. The medical reagent application system of claim 6, wherein the control system is configured to drive the three-dimensional acceleration of said medical reagent by a small-scale medical reagent holding and delivery device comprising at least one dipole(s), immersed in a fluid of a living body, by selecting an angle of each of said dipole(s) in three-dimensional space.

8. The medical reagent application system of claim 6, wherein the control system is configured to drive the three-dimensional acceleration of said medical reagent by a small-scale medical reagent holding and delivery device, said device comprising multiple dipoles oriented along a plurality of different axes allowing the control system to control both a position and three-dimensional orientation of said device immersed in a fluid of a living body, by selecting an angle of each of said dipoles in three-dimensional space.

9. The medical reagent application system of claim 7, wherein the small-scale medical reagent holding and delivery device is of a size at or about the microscale.

10. The medical reagent application system of claim 7, wherein the small-scale medical reagent holding and delivery device is of a size at or about the nanoscale.

11. A medical treatment application system, comprising:

a control system comprising computer hardware and software, remote from an application target within a human or other animal's body, wherein said hardware comprises:

a guidance system comprising a control system actuable radiation source and a magnet, the guidance system being configured to drive a three-dimensional acceleration of an abrasive particle(s) into a target along an at least partially pre-planned path based on varying three-dimensional contours of a surface of said application target; and wherein said radiation source is configured to increase the energy of said abrasive particle(s) above predetermined energy level within said human or other animal's body.

12. The medical treatment application system of claim 11, wherein said abrasive particle comprises a pharmaceutical.

13. The medical treatment application system of claim 11, wherein said abrasive particle comprises a small molecule drug, with a size below 10 nanometers.

14. The medical treatment application system of claim 11, wherein said abrasive particle comprises a small molecule drug, with a size below 5 nanometers.

15. The medical treatment application system of claim 11, wherein said abrasive particle comprises a small molecule drug, with a size below 2 nanometers.

16. The medical treatment application system of claim 11, wherein said abrasive particle(s) comprises a small molecule drug, with a size below 1 nanometer.

17. The medical treatment application system of claim 11, wherein the control system is configured to drive a three-dimensional acceleration of said abrasive particle(s) by a small-scale abrasive particle(s) holding and delivery device, immersed in a fluid of a living body.

18. The medical treatment application system of claim 11, wherein the control system is configured to drive the three-dimensional acceleration of the abrasive particle(s) by a small-scale abrasive particle holding and delivery device, comprising multiple dipoles oriented along a plurality of different three-dimensional axes allowing the control system to control both a position and three-dimensional orientation of said device immersed in a fluid of a living body, by selecting an angle of each of said dipoles in three-dimensional space.

19. A method for treating a human or other animal with an abrasive particle(s), comprising the following steps:

introducing at least one of said abrasive particle(s) into a bodily fluid of said human or other animal;

directing said abrasive particle(s) along a pre-planned three-dimensional path, eroding a three-dimensional surface of a treatment target, and wherein said three-dimensional path is based on a three-dimensional image of said three-dimensional surface.

20. The method for treating a human or other animal with an abrasive particle(s) of claim 19, comprising the following additional step:

causing a plurality of beams of radiation to converge in space at a target volume in which said abrasive particle(s) are located, on, about or within said human or animal's body;

wherein said plurality of beams of radiation create a greater level of energy in said target volume on a proximal side and/or portion of said target volume.

* * * * *